United States Patent [19]

Matson

[11] Patent Number: 4,800,162

[45] Date of Patent: Jan. 24, 1989

[54] METHOD FOR RESOLUTION OF STEROISOMERS IN MULTIPHASE AND EXTRACTIVE MEMBRANE REACTORS

[75] Inventor: Stephen L. Matson, Harvard, Mass.

[73] Assignee: Sepracor, Inc., Marlborough, Mass.

[21] Appl. No.: 33,962

[22] Filed: Apr. 1, 1987

[51] Int. Cl.[4] ............................................. C12P 41/00

[52] U.S. Cl. ................................. 435/280; 435/183; 435/177; 435/179; 435/180; 435/182; 435/135; 435/136; 435/148; 435/155

[58] Field of Search ........................................ 435/280

[56] References Cited

U.S. PATENT DOCUMENTS

| | | | |
|---|---|---|---|
| 3,907,638 | 9/1975 | Uzuki et al. | 435/280 |
| 4,251,631 | 2/1981 | Simon | 435/280 |
| 4,562,152 | 12/1985 | Kleemann et al. | 435/280 |
| 4,565,782 | 1/1986 | Bewick | 435/128 |

Primary Examiner—Sam Rosen
Attorney, Agent, or Firm—Pennie & Edmonds

[57] ABSTRACT

This invention relates to the resolution of racemic mixtures of optically active compounds, including but not limited to the stereochemical purification of chiral organic esters, amides, carboxylic acids, alcohols, and amines. Novel methods utilizing multiphase and extractive enzyme membrane bioreactors are disclosed that selectively produce pure or substantially purified optically active compounds from achiral precursors or mixtures of isomers in which one or several of those isomers are biologically inactive or otherwise lack desirable characteristics.

157 Claims, 16 Drawing Sheets

CHIRAL CENTER ON ALCOHOL MOIETY. ALCOHOL ORGANIC-SOLUBLE.

METHOD FOR RESOLUTION OF STEROISOMERS IN MULTIPHASE AND EXTRACTIVE MEMBRANE REACTORS 1.0 Background of the Invention
  1.1 Significance of Optical Purity
  1.2 Conventional Means of Obtaining Optically Pure Compounds
  1.3 Enzymatic Resolution
  1.4 Enzyme-Catalyzed Bioconversion of Lipophilic Compounds
  1.5 Water-Miscible Cosolvents
  1.6 Multiphase Reaction Systems
  1.7 Enzyme-Catalyzed Reactions in Organic Solvents
  1.8 Enzyme Membrane Reactors
  1.9 Multiphase Membrane Reactors and Separators
2.0 Summary of the Invention
3.0 Brief Description of the Figures
4.0 Detailed Description of the Invention
  4.1 Enzymatic Resolution of Racemic Mixtures
  4.2 Membrane Structure and Enzyme Containment
  4.3 Reaction and Resolution Process Parameters
  4.4 Examples
    4.4.1 Example 1—Naproxen Resolution
    4.4.2 Example 2—Ibuprofen Resolution
    4.4.3 Example 3—Olive Oil Hydrolysis
    4.4.4 Example 4—Olive Oil Hydrolysis
    4.4.5 Example 5—Olive Oil Hydrolysis
    4.4.6 Example 6—Phenoxyacetate Methyl Ester Hydrolysis
    4.4.7 Example 7—Amyl Acetate Hydrolysis
    4.4.8 Example 8—Amyl Acetate Hydrolysis
    4.4.9 Example 9—Ethyl Butyrate Hydrolysis
    4.4.10 Example 10—BTEE Hydrolysis
    4.4.11 Example 11—BTEE Hydrolysis
    4.4.12 Example 12—BTEE Hydrolysis
    4.4.13 Example 13—Resolution of 2-Chloropropionic Acid
    4.4.14 Example 14—Resolution of N-Benzoyltyrosine Ethyl Ester
    4.4.15 Example 15—Resolution of N-Acetyltyrosine Ethyl Ester
    4.4.16 Example 16—BTEE Hydrolysis and Product Enrichment
    4.4.17 Example 17—Glycidyl Butyrate Resolution
    4.4.18 Example 18—Resolution of Butyl 2-Chloropropionate
    4.4.19 Example 19—BTEE Esterification
    4.4.20 Example 20—Ibuprofen Esterification
    4.4.21 Example 21—Phenoxybenzaldehyde Cyanohydrin Hemisuccinate Hydrolysis

1.0 BACKGROUND OF THE INVENTION

Enzymatic resolution procedures have long been known and exploited, especially for the separation of racemic mixtures on the preparative scale. Unfortunately, many chiral compounds of commercial significance are hydrophobic and thus exhibit very low water solubilities. Since enzymes generally operate in aqueous solutions and not organic solvents, it has proven difficult to facilitate the enzyme-catalyzed bioconversion and subsequent separation of selected poorly water-soluble optical isomers.

1.1 Significance of Optical Purity

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (−) or d and l are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

The property of optical activity is due to molecular asymmetry about carbon atoms that are linked to four different atoms or molecules. Where there is only one asymmetric carbon atom, or chiral center as it is sometimes called, there are two possible stereoisomers. Where there are n asymmetric carbons or chiral centers, the number of potential stereoisomers increases to $2^n$. Thus, a molecule with three chiral centers would have eight possible stereoisomers.

While the structural differences between stereoisomers are subtle and of little consequence in ordinary chemical reactions, they may be profound where biological systems are concerned, i.e., if the compounds are utilized in enzyme-catalyzed reactions. Thus, the L-amino acids are metabolized in humans but the corresponding Danalogs are not, and only D-glucose can be phosphorylated and processed into glycogen or degraded by the glycolytic and oxidative pathways of intermediary metabolism. Similarly, beta blockers, pheromones, prostaglandins, steroids, flavoring and fragrance agents, pharmaceuticals, pesticides, herbicides, and many other compounds exhibit critical stereospecificity. In the field of pesticides, Tessier [Chemistry and Industry, Mar. 19, 1984, p. 199] has shown that only two of the eight stereoisomers of deltamethrin, a pyrethroid insecticide, have any biological activity. The same statement concerning the concentration of bioactivity in a single isomer can be made about many other pesticides, including the phenoxypropionates and halopropionate derivatives, each containing one chiral center and existing in the form of two optical isomers.

Stereochemical purity is of equal importance in the field of pharmaceuticals, where 12 of the 20 most prescribed drugs exhibit chirality. A case in point is provided by naproxen, or (+)-S-2-(6-methoxy-2-naphthyl)-propionic acid, which is one of the two most important members of a class of 2-aryl-propionic acids with non-steroidal anti-inflammatory activity used, for instance, in the management of arthritis. In this case, the S(+) enantiomer of the drug is known to be 28 times more therapeutically potent than its R(−) counterpart. Still another example of chiral pharmaceuticals is provided by the family of beta-blockers; the L-form of propranolol is known to be 100 times more potent than the D-enantiomer.

Synthesis of chiral compounds by standard organic synthetic techniques generally leads to a racemic mixture which, in the aggregate, may have a relatively low specific bioactivity since certain of the stereoisomers in the mixture are likely to be biologically or functionally inactive. As a result, larger quantities of the material must be used to obtain an effective dose, and manufacturing costs are increased due to the co-production of stereochemically "incorrect" and hence, inactive ingredients.

In some instances, certain isomers may actually be deleterious rather than simply inert. For example, the D-enantiomer of thalidomide was a safe and effective sedative when prescribed for the control of morning sickness during pregnancy. However, its L-thalidomide counterpart was discovered to be a potent mutagen.

1.2 Conventional Means of Obtaining Optionally Pure Compounds

Methods are available for stereoselective synthesis. For example, a synthetic pathway to optically pure deltamethrin [(1R,3R)-3-(2,2-dibromovinyl)-2,2-dimethyl cyclopropane carboxylic acid] has been developed, but the process is lengthy, complex and costly [Tessier, J., *Chem. and Ind.*, Mar. 9, 1984, p.199]. Moreover, a synthetic scheme capable of producing one specific enantiomer cannot be applied in a general way to obtain other optically active compounds. What is needed is a generalized approach to the resolution of racemic mixtures produced by ordinary chemical reactions, and a number of approaches have been used.

As the term "racemic mixture" is used herein, it is intended that it refer to a mixture of at least a first and second stereoisomer in any proportions. Further, it is intended that the term "resolution" as used herein will refer to separation of a first racemic mixture into second and third mixtures wherein the proportions of the two stereoisomers in the second and third mixtures are different from that in the first racemic mixture, the proportion being greater in one and necessarily smaller in the other.

A widely used approach has been the selective precipitation of desired compounds from racemic mixtures. For example, Yoshioka et al. [U.S. Pat. No. 3,879,451] treated a mixture of (±)-cis- and (±)-trans-chrysanthemic acids with an optically active aromatic amine and recovered the amine salts of (±)-cis- and (±)-trans-chrysanthemic acids by crystallization. Paven et al. [U.S. Pat. No. 4,257,976] resolved D,L-cis-chrysanthemic acid and D,L-transchrysanthemic acid by treating the mixtures with L or D N-methyl-ephedrine to form the corresponding salts, which were then hydrolyzed after isolation to produce the resolved acids. Halmos [U.S. Pat. No. 4,151,198] treated a mixture of N-acyl-D,L(±)-phenylalanine isomers with D(-)-2-(2,5-dimethylbenzylamino)-1-butanol to obtain a crystalline salt, from which N-acyl-L(+)-phenylalanine could be recovered. Kameswaran [U.S. Pat. No. 4,454,344] isolated dextrorotatory 2-(p-difluoromethoxyphenyl)-3-methylbutyric acid by treating the racemic acid with an optically active amine. The S(+)-enantiomer of naproxen can be obtained by stereoselective crystallization of a diastereomeric salt formd with an amine resolving agent such as cinchonidine, glucamine, or N-methylglucamine [Harrison, I.T. et al., J. Med. Chem., 13:203 (1970); Felder, E. et al., U.K. Patent Appl. No. GB2025968A (1980)].

In some cases, a two-step method has been used, as when Dannenberg et al. [U.S. Pat. No. 4,285,884] resolved racemic D,L-alpha-aminocarboxylic acids by first treating the mixture with an aromatic o-hydroxy aldehyde to obtain an azomethine derivative. This derivative was then immediately treated with an optically active amine base to produce a salt which was isolated. By subjecting the salt to acid hydrolysis, the desired alpha-aminocarboxylic acid isomer was obtained.

The above procedures successfully resolved racemic mixtures because treatment of the mixtures with optically pure reagents produced diastereomers which, unlike the initial racemic compounds, have different physical properties. Thus, fractional crystallization or other physical means may be employed to separate diastereomeric compounds.

Separation of diastereomers can also be carried out by chromatography. For example, Pollock et al. [J. Gas Chromatogr. 3:174 (1965)]have resolved diastereomeric amino acids by gas chromatography. Mikes et al. [J. Chromatogr. 112:205 (1976)] have used liquid chromatography to resolve diastereomeric dipeptides. In most cases, the optically pure reagents have been in the stationary phase during chromatographic separation, but they may also be used in elutants. Hare et al. [U.S. Pat. No. 4,290,893] have used liquid chromatography to resolve racemic mixtures that were treated with aqueous elutants containing optically pure reagents and metal cations; resolution occurred because the resulting diastereomeric complexes had different partition coefficients in the chromatographic system.

1.3 Enzymatic Resolution

All of the methods described to this point have relied upon the availability of suitable optically pure reagents, but such reagents are often not available or else their use is prohibitively expensive. In an alternative approach, enzymatic resolution techniques have been developed. Many different classes of enzymes have been used for the resolution of stereoisomers on a preparative scale, including hydrolases (especially the lipases and esterases such as chymotrypsin), lyases, and oxidoreductases (e.g., amino acid oxidases and alcohol reductases). Generally speaking, enzymes for use in resolutions should ideally exhibit broad substrate specificity, so that they will be capable of catalyzing reactions of a wide range of "unnatural" substrates, and a high degree of stereoselectivity for catalyzing the reaction of one isomer to the exclusion of others.

The hydrolases (e.g., lipases and esterases) are among the more attractive enzymes for use in resolutions, because they are commercially available at reasonable cost, they do not require expensive cofactors, and some of them exhibit reasonable tolerance to organic solvents. Additionally, chiral chemistry often involves alcohols, carboxylic acids, esters, amides, and amines with chiral carbons, and carboxyl hydrolases are preferred choices as stereoselective catalysts for reactions of such species [Cambou, B. and A. M. Klibanov, *Biotechnol. Bioeng.*, 26:1449 (1984)].

For instance, enzymatic treatment has been applied to the resolution of racemic mixtures of amino acid esters. Stauffer [U.S. Pat. No. 3,963,573] produced optically pure N-acyl-L-methionine by treating N-acyl-D,L-methionine ester with microbial proteases and separating the product acid from the reaction mixture. Similarly, Bauer [U.S. Pat. No. 4,262,092] prepared optically pure D-phenylalanine ester by subjecting a racemic mixture of N-acyl-D,L-phenylalanine ester to the action of a serine protease, separating the unaffected N-acyl-D-phenylalanine ester, and removing the N-acyl and ester groups. Clement and Potter [*J. Chem. Ed.*, 48:695 (1971)] employed chymotrypsin to resolve phenylalanine, and Matta et al. [*J. Org. Chem.*, 39:2291 (1974)] used the same enzyme in the resolution of precursors of the drug 3-(3,4-dihydroxyphenyl)alanine or dopa.

Amino acid resolution with chymotrypsin involves first forming the acyl and ester derivatives by standard procedures and then subjecting the racemic mixture to enzymatic hydrolysis. The inert, poorly water-soluble D-ester is generally separated from the much more water-soluble N-acylated L-amino acid product by selective extraction with an organic solvent. The free L- and D-amino acids can be recovered (e.g., by acid hydrolysis) if desired, and the unwanted isomer racemized and recycled. Alternatively, separation of reaction products from enzymes has been facilitated by attaching the enzyme to a solid support which could be removed by centrifugation or packed into a column through which the racemic mixtures were passed. Matson [Membrane Reactors, Doctoral Dissertation, University of Pennsylvania (1979)] used chymotrypsin immobilized on a membrane to selectively cleave the L-amino acid ester linkage in a racemic aqueous mixture of N-acetyl-D,L-tyrosine ethyl ester. Scollar et al. [*Biotech. Bioeng.*, 27:247 (1985)] employed acid phosphatases in the preparative-scale resolution of D,L-threonine.

Enzymes have also been explored for the resolution of classes of compounds other than the amino acids discussed above. In particular, Cambou and Klibanov [*Biotech. Bioeng.*, 26;1449 (1984)] examined the use of lipase immobilized in porous beads for the enzymatic resolution of mixtures of (R,S)-2-(p-chlorophenoxy)-propionic acid (whose R isomer is an herbicide) and various esters thereof. Their studies showed that the immobilized lipase could in principle resolve the mixtures by enzymatic hydrolysis or transesterification. In the case of the biphasic hydrolysis reaction, the differing solubility properties of the acids and esters involved required the dispersion and agitation of mixtures containing the immobilized solid-phase enzyme, an aqueous buffer, and the water-immiscible organic phase containing solvent and reactant—a relatively inefficient process.

Enzymes have been applied to the resolution of optical isomers of insecticides. For instance, Mitsuda et al. [Eur. Patent Appl'n. Publ. No. 0 080 827 A2] contacted the racemic acetic acid ester derivative of (R,S)-alpha-cyano-3-phenoxybenzyl alcohol with stereoselective esterases of microbial and animal origin in biphasic systems (i.e., aqueous/organic dispersions). The S-ester was selectively hydrolyzed, thereby producing (S)-(−)-alpha-cyano-3-phenoxybenzyl alcohol, the alcohol moiety of the pyrethroid family of insecticides. In related work on optically purified pyrethroids, Mitsuda et al. [U.S. Pat. No. 4,607,013] employed microbial esterases for the optical resolution of racemic (+)-4-hydroxy-3-methyl-2,2,-propynyl-2-cyclopentenone; the ester derivative of the (+)-isomer of this compound has several times the pesticidal activity of its (−)-isomer counterpart. Klibanov et al. [U.S. Pat. No. 4,601,987] resolved racemic 2-halopropionic acids by means of lipase-catalyzed esterification reactions conducted in organic media. The resolved 2-halopropionic acids so prepared can be employed in the synthesis of 2-phenoxypropionic acids and their esters; these are widely used as herbicides, with only the R optical isomers exhibiting biological activity.

Additional examples can also be provided of the state-of-the-art of enzyme-mediated resolution as applied to the production of optically purified pharmaceuticals. Sih [U.S. Pat. No. 4,584,270] has disclosed enzymatic means for the production of optically pure (R)-4-amino-3-hydroxybutyric acid, a key intermediate in the preparation of L-carnitine. Other microbial- or enzyme-mediated approaches to L-carnitine manufacture have been disclosed by Aragozzini et al. [Biotechnol. Letters, 8:95 (1986)] and by Yokozeki et al. [Eur. Patent Appl'n. Publ. No. 0 122 794 A2]. Sih [Tetrahedron Letters, 27:1763 (1986)] has also described the application of microbial lipases to the stereoselective hydrolysis in biphasic reaction media of ester derivatives of (R,S)-naproxen, resulting in production of the partially optically purified (S)-naproxen acid. Finally, certain optically pure D-amino acids (in particular, the D-aryl-glycines such as phenylglycine and 4-hydroxyphenylglycine) are used as side chains in the manufacture of semi-synthetic penicillins and cephalosporins. Schutt et al. [Biotechnol. Bioeng., 27:420 (1985)] have subjected racemic mixtures of such nonpolar N-acyl-D,L-amino acid esters to the hydrolytic action of subtilisin in two-phase systems for the purpose of obtaining optically purified D-amino acids.

1.4 Enzyme-Catalyzed Bioconversion of Lipophilic Compounds

For the most part, attempts by biochemical engineers to exploit enzymatic catalysis in large-scale industrial biotransformations have focused on the use of enzymes in aqueous reaction systems containing water-soluble substrates. The conversion of glucose to fructose by glucose isomerase affords one such example. However, enzyme are also used in the bioconversion of lipophilic (i.e., sparingly water-soluble) substrates. For example, many of the structurally complex pharmaceutical compounds and agricultural chemicals are prime candidates for enzymatic bioconversions. In particular, such complex molecules are often chiral. Unfortunately, many of these complex molecules exhibit very low water solubilities, and it is generally impractical to feed such poorly water-soluble substrates to conventional immobilized enzyme bioreactors in homogeneous, aqueous solution for several reasons. On the one hand, enzyme reactors sized to deal with such dilute reaction systems would be inordinately large, and recovery and concentration of bioproducts from such dilute aqueous process streams would often prove prohibitively expensive. Several prior-art approaches have been explored for making enzyme-catalyzed conversions of water-insoluble substrates more efficient.

1.5 Water-Miscible Cosolvents

A number of water-miscible organic cosolvents have been used to prepare homogeneous substrate/enzyme solutions in cases where lipophilic substrates (e.g., steroids) are poorly water-soluble [Tanaka, A. and S. Fukui, "Bioconversion of Lipophilic Compounds by Immobilized Biocatalysis in the Presence of Organic Solvents," pp. 149–176 in Enzymes and *Immobilized Cells in Biotechnology*, A. I. Laskin, ed., Benjamin/Cummings Publishing Co., Menlo Park, CA (1985); Klibanov, A. M. et al., Biotechnol. Bioeng., 19:1351 (1977)]. Organic cosolvents useful for this purpose have included the lower alcohols (especially methanol and ethanol), acetone, dimethyl formamide, and dimethyl sulfoxide. Unfortunately, miscibility is usually achieved with organic cosolvents only at the price of reduced enzyme activity, selectivity, and/or stability. Moreover, such systems are seldom hydrophobic enough to dissolve very lipophilic substrates. For these reasons the use of cosolvents to facilitate enzyme-catalyzed bioconversions of lipophilic substrates is limited.

1.6 Multiphase Reaction Systems

Certain of these problems can be avoided (at the expense of introducing new ones) by conducting enzyme-catalyzed bioconversions of sparingly water-soluble substrates in multiphase systems [Lilly, M., J. Chem. Tech. Biotechnol., 32:162 (1982); Carrea, G., Trends in Biotechnol., 2:102 (1984)]. On the one hand, the enzymatic reaction may be conducted in a two-phase or "biphasic" system in which free enzyme is dissolved in a continuous, aqueous phase and substrate (and often products) are present in a separate, immiscible organic phase dispersed within the aqueous phase. Alternatively, the aqueous phase may be dispersed within a continuous organic phase. In other cases where it is desirable to immobilize the enzyme on a high-surface-area support in order to facilitate its recovery and reuse, a triphasic reaction scheme may be employed, at least in principle. In three-phase systems, the water-insoluble substrate is generally supplied in an organic phase (with or without added organic solvent), with the organic phase being dispersed in a continuous aqueous phase. The enzyme is then immobilized on or within a third, solid phase, and the three phases are contacted in a stirred vessel or packed bed. In the most common situation, both substrates and products will be found in the organic phase [Brink, L. E. S. and J. Tramper, Biotechnol. Bioeng., 27:1258 (1985)].

Many pharmaceuticals and agricultural chemicals exhibit very low solubilities in water, and accordingly a number of the enzyme-mediated optical resolutions of such compounds as cited above were conducted under multiphasic reaction conditions. In one such example, Cambou and Klibanov [Biotechnol. Bioeng., 26:1449 (1984)] investigated the lipase-mediated resolution of 2-(p-chlorophenoxy)propionic acid, derivatives of which are herbicides. They found yeast lipase (*Candida cylindracea*) to be highly stereospecific in the resolution of (R,S)-2-(p-chlorophenoxy)-propionic acid when used to catalyze hydrolysis of simple esters (e.g., the methyl ester) of the racemic acid. Because these esters are substantially water-insoluble, the resolution procedure was necessarily conducted in a multiphase reaction system wherein three separate phases were present: namely, an organic phase containing the racemic reactant ester, an aqueous buffer, and the immobilized enzyme. Typically, the lipase was immobilized by entrapment and adsorption on high-surface-area Chromosorb or titania beads, and this solid-phase enzyme and the organic phase containing the reactant were dispersed within the aqueous phase by vigorous shaking to produce an emulsion. By this means, Cambou and Klibanov produced the desired R-acid in hundred gram quantities in 85% yield and at 97% purity; the enantiomeric excess of R-acid over S-ester was found to be 96%.

Other examples of multiphase, biocatalytic reactions include the enzymatic hydrolysis of triglycerides (e.g., olive oil) to fatty acids [Linfield, W. M. et al., JAOCS, 61:191 (1984)]and the microbial production of optically active epoxides (e.g., 1,2-epoxyoctane) from alkenes [van der Meer, Chem. Eng. Sci., 41:607 (1986)].

Unfortunately, multiphasic reaction systems also suffer from a number of drawbacks, particularly on the industrial scale. For example, scale-up and reliability problems are frequently associated with the processing of dispersions and emulsions, and continuous operation and pH control (especially in hydrolytic reactions) are difficult to achieve. Additionally, the phases must be separated before product can be recovered, and excessive interphase mass transfer resistances are often encountered, associated with diffusion of the poorly soluble substrate in the aqueous phase.

Certain of these limitations of conventional multiphase enzymatic reaction systems have been discussed previously in a general way [Matson, S. L., pp. 597–610 in *The World Biotech Report* 1985—Vol. 1: *Europe*, proceedings of Biotech 85 Europe, Geneva, May, 1985; Michaels, A. S. and S. L. Matson, Desalination, 53:231 (1985)].

1.7 Enzyme-Catalyzed Reactions in Organic Solvents

Another approach to the use of enzymes in conjunction with water-insoluble substrates involves conducting the reaction in substantially water-free organic reaction media [Zaks, A. and A.M. Klibanov, Science, 224:1249 (1984); Butler, L. G., Enzyme Microb. Technol., 1 253 (1979)] or in the presence of reversed micelles containing entrapped enzymes [Han, D. and J. S. Rhee, Biotechnol. Bioeng., 28:1250 (1986)]. While some limited success has been achieved with these approaches [e.g., Klibanov, A. M. and G. Kirchner, U.S. Pat. No. 4,601,987], they are not very general. In particular, many enzymes are altogether inactive in neat or water-saturated organic solvents, and those that do retain some activity often exhibit altered selectivity or impaired stability. Additionally, control of the pH of enzyme operation is problematic in organic solvents, and it is difficult to achieve efficient (i.e., molecular-level) dispersion of insoluble enzymes in organic solvents. Finally, hydrolytic reactions involving water as a reactant or product obviously cannot be conducted on a large-scale, continuous basis in substantially anhydrous reaction media.

What is needed is a better immobilized-enzyme reactor design and process for the efficient conduct of enzyme-catalyzed conversions of poorly water-soluble substrates.

1.8 Enzyme Membrane Reactors

In recent years, several types of membrane reactors have been explored for the conduct of enzyme-catalyzed bioconversions. Among the simplest is an enzyme continuous-stirred-tank/ultrafiltration (CSTR/UF) reactor wherein an aqueous solution of an enzyme confined within a continuous stirred tank reactor (CSTR) is continuously circulated through an ultrafiltration module, from which enzyme-free ultrafiltrate is continuously removed while fresh substrate for the enzymatic conversion is continuously fed to the reactor in aqueous solution. This results in continuous generation and isolation of the enzymatically transformed product, without loss of enzyme. A number of nutritionally important amino acids and 2-hydroxy acids have been synthesized or optically resolved, some on an industrial scale, in Japan and Germany via enzymatic reactions that are conducted in homogeneous, single-phase CSTR/UF membrane reactors [Michaels, A. S. et al., J. Memb. Sci., 15:118 (1983); Jandel, A.-S. et al., Eur. J. Appl. Microbiol. Biotechnol., 15:59 (1982); Wichmann, R. et al., Annals N.Y. Acad. Sci., 434:87 (1984)]. In a variant of the above approach, continuous enzymatic transformations have been carried out within a membrane ultrafiltration cell by allowing an enzyme to concentrate by polarization on the upstream membrane surface [Drioli, E. and V. Scardi., J. Memb. Sci., 1:237 (1976); Greco, G. et al., Eur. J. Appl. Microbiol.

Biotechnol., 8:249 (1979); Greco, G. and L. Gianfreda, Biotechnol. Bioeng., 23:2199 (1981)]. Upon continuous ultrafiltration of an aqueous solution of substrate, the latter is transformed to product in transit across the enzyme gel layer residing atop the membrane, and an aqueous product stream emerges from the opposite membrane surface as the permeate.

A somewhat different membrane/immobilized enzyme reactor concept involves the confinement of a concentrated aqueous solution of enzyme to the shell-side of a hollow-fiber-bundle ultrafilter, with aqueous substrate solution passed continuously through the lumens of the fibers [Waterland, L. R. et al., Aiche J., 20:50 (1979); Michaels, A. S. et al., U.S. Pat. No. 4,440,853; Breslau, B. R., U.S. Pat. No. 4,266,026]. Kinetically limited conversions were achieved in this manner. Since then, many hollow-fiber-immobilized enzyme reactor configurations have been explored. Additionally, enzymes have been covalently attached to high-internal-surface-area microporous membranes for the purpose of effecting enzyme-catalyzed reactions of aqueous-phase reactants to aqueous-phase products [Simon, S., U.S. Pat. No. 4,251,631; Gregor, H. P., U.S. Pat. No. 4,033,822].

In some cases, it has proven preferable to utilize the entire catalytic machinery of the cell rather than an individual enzyme to effect a biological conversion. In hollow fiber cell culture and biocatalysis, one of the compartments in the membrane device is loaded with whole cells, and the device subsequently is perfused with an aqueous feed containing substrate and nutrients [Michaels, A. S. et al., U.S. Pat. No. 4,440,853; Inloes, D. S. et al., Biotechnol. Bioeng., 25:2653 (1983); Hopkinson, J., Biotechnology, 3:225 (1985)]. Where the cells are viable, means for the supply of oxygen and removal of carbon dioxide may be required [Kornfield, J. et al., Biotechnol. Progress, 2 98 (1986)].

1.9 Multiphase Membrane Reactors and Related Processes

Membranes have been used as enzymatic reactors in multiphase reaction systems in essentially two contexts: (i) hollow-fiber cell culture and fermentation methods and apparatus, and (ii) multiphase enzymatic catalysis of water-immiscible but achiral reactants and achiral products.

Examples of hollow-fiber cell culture abound. Typically, the spongy fiber wall in a hollow-fiber membrane module is loaded with viable (but ideally "resting") cells, and a nutrient solution is passed through the bores of the hollow fibers. In some instances, hollow-fiber culture systems have been operated in a biphasic mode. For example, viable cells have been entrapped within the porous membrane wall of a hollow fiber device, an aqueous nutrient stream has been passed through the fiber lumen, and a gaseous stream of oxygen has been passed concurrently through the outer shell compartment [Michaels, A. S. et al., U.S. Pat. No. 4,440,853]. Nutrients diffused from the aqueous feed of that device into the cell compartment, where they were ultimately converted to metabolites and other products which diffused back into the aqueous stream in the lumen and so exited the cell culture device. In addition to supplying oxygen to the cells, a gaseous process stream can also serve to carry gaseous waste products (e.g., carbon dioxide) out of the device.

A number of variations of this basic hollow-fiber cell culture method and apparatus exist. [For example, J. P. Tharakan and P.C. Chau Biotechnol. Bioeng., 18:329 (1986)] have described a radial-flow hollow-fiber cell culture device wherein cells are located outside of the hollow fibers, aqueous nutrients are supplied to the shell-side compartment containing the cells, and gaseous nutrients (i.e., $O_2$) are fed to the bores of the fibers. In operation, a convective, radial flow of aqueous nutrients is established across the cells and subsequently across the hollow-fiber walls, with the flow of gas through the fiber lumen serving also to carry the spent aqueous medium containing the desired products out of the device.

Cho and Shuler describe a multimembrane bioreactor containing four layers of gas, cells, nutrient, and solvent that are separated by three membranes: two hydrophobic and one hydrophilic. None of the membranes is enzyme-activated [Cho, T. and M. L. Shuler, Biotechnol. Progress, 2:53 (1986)]. This multimembrane system has been used in an extractive fashion to remove inhibitory ethanol from fermenting cells of the yeast *Saccharomyces cerevisiae*.

All of the above methods for hollow-fiber cell culture and fermentation are readily distinguished from the process of the present invention. In none of these references is the production of stereochemically purified compounds by enzymatic means an objective of the fermentation or cell culture processes. Instead of employing specific enzymatic activities for stereoselective biotransformations of chiral compounds, the only disclosure is the use of viable whole cells in fermentative or cell culture operations. Separation of optical isomers in a racemic mixture or production of chiral products from achiral precursors is neither intended nor accomplished in these systems.

Various lipids or triglycerides, e.g., olive oil, and fatty acids have also been subjected to membrane-medicated reactions. Kerkhof has discussed the enzymatic hydrolysis of lipids in a membrane reactor wherein a water-immiscible triglyceride is fed inside regenerated-cellulose hollow fibers coated with an enzyme gel layer, and water is supplied to the outside of the fibers [Kerkhof, P. I. A. M., et al., "Enzymatic Hydrolysis of Lipids in a Membrane Reactor," a poster presented at the International Membrane Technology Symposium, Lund, Sweden, May 28-30, 1985]. Others have studied essentially identical processes for lipid hydrolysis [Molinari, R. and E. Drioli, Proc. Nat. Congr. Ind. Chem. Div. Sci., Siena, June, 10–12, 1985]. Japanese investigators have explored the enzymatic synthesis of triglycerides [Yamane, T. et al., Annals N.Y. Acad. Sci., 434:558 (1984)] in a membrane reactor system wherein opposite surfaces of a separating membrane are in contact with aqueous and organic phases containing reactants and products. However, in this system the lipase enzyme employed is dissolved in the aqueous phase (i.e., in Yamane et al.).

2.0 SUMMARY OF THE INVENTION

Methods and apparatus are provided for the resolution of racemic mixtures and for the enzymatic synthesis from achiral precursors of optically active organic acids, alcohols, esters, amides, amines, nitriles, hydantoins and other chiral compounds including many pharmaceuticals, fragrance and flavoring agents, agriculturals chemicals (e.g., pesticides and herbicides), and other chemical classes. Stereoselective reactions are carried out using enzyme-containing multiphase and extractive membrane bioreactors, multiphase solvent systems, and membrane reactor operating conditions such that the reaction is conducted in an efficient manner and the products are cleanly isolated from the reactants. Depending upon the chiral character of the racemic mixture, the product streams so obtained contain either optically pure compounds or materials substantially enriched in particular isomeric forms.

More specifically, this invention is particularly useful in the conduct of enzymatic resolutions and chiral syntheses of compounds that are poorly water-soluble or that are produced via product-inhibited reactions. Racemic mixtures that may be processed by this invention include mixtures of isomers of chiral organic alcohols, acids, esters, amines, amides, and other compounds. Hydrolytic enzymes particularly useful in the practice of this invention include the lipases, carboxyl esterases, and amidases. Achiral precursors which, by the process of the present invention, can be biotransformed into valuable chiral products include hydantoins and amino nitrile compounds, which can stereoselectively be converted into such valuable products as amino acids (e.g., D-amino acids and methyl dopa) and amino amides.

For purposes of organizing the description of the process of the present invention, it is useful to discuss the "multiphase" and "extractive" membrane reactor processes separately, since the specific applications of the present invention conveniently fall into these two categories. As utilized herein a membrane reactor process is referred to as "multiphase" when a key reactant is fed via a water-immiscible organic phase—and as an "extractive" one when one or more key reactants is fed to the process in an aqueous solution. However, it will be seen that the construction and operation of these "multiphase" and "extractive" membrane reactors and stereoisomer separation/synthesis processes are identical in most important respects.

The enzyme-activated membrane in the multiphase membrane reactor process of this invention will typically consist of a porous and hydrophilic (i.e., water-wet) membrane which is suitably activated by incorporation of an appropriate enzyme within it or on one or more of its surfaces by various means. One surface of this enzymatically active membrane is placed in contact with a first process stream, the feed stream, which stream typically contains a sparingly water-soluble (i.e., water-immiscible) substrate for the enzyme. Typically, this water-immiscible (organic-based) feed stream may contain only the reactant in the form of a neat organic liquid, or it may consist of a poorly water-soluble, organic-soluble reactant dissolved in a water-immiscible organic solvent that serves as a carrier fluid. Other co-reactants may also be present in this feed stream.

Concurrently, the second surface of the enzymatically active membrane is contacted with an aqueous process stream, which stream serves one or more of the following purposes: to supply or remove any water of reaction; to provide means for control of reaction pH (and in some cases access to enzyme contained in the membrane); and to provide means for removal of water-soluble reaction products. When properly operated, the aqueous/organic phase boundary will reside at the surface of the water-wet enzyme-activated membrane that is in contact with the water-immiscible organic feed stream, and a substantially aqueous environment will be provided for operation of the enzyme in the hydrophilic, water-wet membrane. Two inlet (i.e., feed) and two outlet (i.e., product) streams will thus be supplied to and removed from the process of this invention, respectively, and the membrane reactor module will thus necessarily be configured with two inlet and two exit ports. One inlet/outlet pair of these ports will be devoted to the supply and withdrawal of the organic-phase process stream, while the other pair will be dedicated to supply and removal of the aqueous process stream.

With hydrophilic or water-wet enzyme-activated membranes, this organic process stream is preferably placed under a small positive pressure relative to the aqueous process stream in contact with the opposite surface of the membrane. This resulting small organic-to-aqueous pressure difference across the membrane serves to prevent the ultrafiltrative flow of a portion of the aqueous process stream across the membrane. At the same time, by operating the process in this manner the organic phase will be prevented from intruding into the pores of the water-wet enzyme membrane by the capillary forces acting at the surface of the membrane in contact with it.

In the practice of the invention herein, a poorly water-soluble, preferentially organic-soluble reactant is fed to the membrane reactor in a water-immiscible organic process stream, where it is contacted with a first surface of the enzymatically active membrane. Molecules of the reactant subsequently diffuse to the aqueous/organic interface located at the first surface of the membrane, where they partition into aqueous regions of the membrane and undergo enzyme-catalyzed conversion to products. Where at least one of the reaction products exhibits significant water-solubility, and especially where it is much more water-soluble than the reactant, this product species diffuses out of the membrane and into the aqueous process stream in contact with the second surface of the enzymatically active membrane, to be subsequently removed from the reactor and ultimately recovered in high stereochemical purity. Unreactive species in the feed stream (e.g., organic-soluble enantiomers in a racemic feed mixture towards which the enzyme does not exhibit activity) remain in the organic phase, and are thereby separated from water-soluble enzymatic reaction products.

In summary, the enzyme-activated membrane in this continuous multiphase bioreactor process serves in three roles: namely, as a high-surface-area organic/aqueous phase contactor, as an organic/aqueous phase separator, and as an interfacial biocatalyst. By placing a hydrophilic membrane at the interface between immiscible aqueous and organic process streams in a membrane module characterized by a high membrane area packing density, it is possible to provide a large organic/aqueous and fluid/membrane contact area without the necessity of dispersing one immiscible phase within the other as is more conventional practice.

In this manner, the multiphase membrane reactor addresses limitations of dispersed-phase systems related to their lack of predictability, poor reliability, and not-very-scaleable performance. Moreover, the multiphase and extractive membrane reactor process avoids the difficulty of dealing with troublesome emulsions and the need to continuously separate the three immiscible phases (i.e., organic, aqueous, and solid) from one another prior to product recovery and/or reactant recycle. A further advantage of membrane reactor processing is that continuous operation (as opposed to batch processing) is made more feasible.

Yet another important aspect of this invention is its provision of means for direct contact between the reactant-containing organic phase and the enzyme-containing solid phase, without intercession of the bulk aqueous phase that is present in conventional dispersed-phase reactor designs (See FIG. 3). In particular, significant aqueous-phase mass transfer limitations that plague conventional dispersed-phase catalytic reactors can be avoided, and the productivity and efficiency of the catalytic conversion are thereby enhanced. Additionally, unconverted water-insoluble, organic-soluble reactants, co-products or byproducts, and non-reactive species may be removed in the water-immiscible organic process stream, while water-soluble and organic-insoluble reaction products can be removed in a second process stream. This constitutes separation of water-soluble product from other lipophilic components of the reaction system. Finally, by controlling flowrate or phase ratios of the aqueous and organic process streams, it is frequently possible to enrich a reaction product as well, removing this aqueous-phase product species at a concentration higher than the concentration of its organic-phase precursor or reactant in the feed stream.

Typically, the membrane-immobilized enzyme used in this invention will stereoselectively convert one reactive stereoisomer in a racemic (R & S) feed mixture of water-insoluble feed isomers to a water-soluble product isomer (R or S) of altered chemical composition. This water-soluble product isomer will exit the enzyme membrane reactor via the aqueous process stream, while the unreactive water-insoluble reactant isomer (S or R) in the racemic feed will leave the reactor via the organic process stream. The overall result is that these two species with different stereoconfigurations will be isolated from one another and thereby at least partially optically enriched. In this manner, optical resolution of a racemic feed mixture can be accomplished in a multiphase membrane reactor. In the same way, the multiphase enzyme membrane reactor process can produce and concurrently isolate a water-soluble organic product stereoisomer in the aqueous process stream exiting a multiphase membrane reactor from an organic-soluble, relatively water-insoluble achiral precursor that remains in the organic process stream.

The extractive membrane reactor process of this invention is similarly useful in the resolution of racemic mixtures and the enzymatic synthesis of chiral products from achiral precursors. This embodiment of the process is particularly appropriate in situations where the enzymatic reaction is inhibited either kinetically or thermodynamically by modest concentrations of the product, or where the product of reaction has limited chemical stability at reaction conditions. In particular, the extractive membrane reactor addresses limitations of low conversion and catalyst productivity that are associated with thermodynamically unfavorable biosynthetic reactions and with bioconversions catalyzed by product-inhibited, feedback-controlled enzymes.

The enzyme-activated membrane of the extractive membrane reactor process will typically be hydrophilic and microporous, as it is in the multiphase membrane reactor process embodiment of this invention, and it is used similarly insofar as it is contacted on opposite sides with substantially immiscible aqueous and organic process streams. Thus, the enzyme-activated membrane in both the extractive and the multiphase membrane reactor process embodiments serves both to provide high-surface-area contact between these immiscible process streams as well as to separate them.

However, in the case of the extractive membrane reactor process, either an achiral precursor or the stereoisomers in a racemic feed mixture presented to the enzyme-activated membrane will typically be preferentially water-soluble as opposed to organic-soluble as in the case of the multiphase membrane reactor embodiment of the process. Accordingly, the feedstream supplied to the extractive membrane reactor process will be aqueous rather than organic. The chiral enzymatic reaction product formed in an extractive membrane reactor process will typically be more organic soluble than water-soluble and, thus, it will partition for the most part into the organic process stream and be carried out of the reactor via that stream.

In operation of the extractive membrane reactor process, at least one preferentially water-soluble, organic-insoluble reactant (e.g., a stereoisomer in a racemic mixture or an achiral precursor) is supplied to the enzyme-activated membrane via an aqueous feed stream. This water-borne reactant subsequently diffuses into the hydrophilic, water-wet membrane, where it encounters an enzyme that stereoselectively catalyzes its conversion to a product, perhaps in conjunction with other coreactants. At least one of the reaction products so produced will exhibit significant solubility in the organic phase. Thus, this species will diffuse to the aqueous/organic interface that is located at the surface of the enzyme-activated membrane in contact with the organic phase, where it will preferentially partition into the water-immiscible organic process stream for subsequent removal from the reactor.

By virtue of the selective removal of an organic-soluble and inhibitory and/or unstable reaction product into the organic process stream of the extractive membrane reactor process, the enzymatic reaction system is made more productive. In an extractive membrane reactor, the inhibitory or unstable reaction product is produced in close proximity to the organic extractant. By minimizing diffusional distances, the membrane process improves product extraction efficiency relative to the usual situation with prior-art dispersed-phase reaction systems of the type show in FIG. 10. In these prior-art systems, where enzymes are immobilized on particulate supports, a significant mass transfer resistance, associated with the intervening bulk aqueous phase, can impede the efficient removal of reaction product from the enzyme phase into the organic extractant. The fact that the inhibitory reaction product is produced in an enzyme-activated membrane in close proximity to the organic extractant improves the product extraction efficiency (by minimizing its aqueous-phase diffusion distance) relative to conventional dispersed-phase reaction systems with enzymes immobilized on particulate supports. By virtue of the stereoselectivity of the enzyme catalyst, at least one of the product streams withdrawn from the process will be enriched in a particular stereoisomer and largely separated from other stereoisomers, achiral precursors, and/or achiral coreactants and byproducts.

In this fashion, multiphase and extractive enzyme membrane reactor processes can be employed to efficiently produce stereochemically purified or optically enriched products from racemic and optically inactive feed mixtures or from achiral precursors, even in situations where the limited water-solubility of reactants or the product-inhibited nature of the reaction would preclude the efficient operation of prior-art enzymatic resolution technology.

3.0 BRIEF DESCRIPTION OF THE FIGURES

This invention may be more readily understood by reference to the following detailed description of the invention and figures, in which FIG. 1 is a schematic representation of a method for the resolution of a racemic mixture of organic-soluble esters, in which the mixture fed in an organic solvent stream onto one side of an enzyme-activated membrane is stereospecifically hydrolyzed by the enzyme, and the optically enriched organic acid (and water-soluble alcohol co-product) thereby produced are removed by a countercurrent aqueous process stream fed onto the other side of the membrane;

Figure 5:
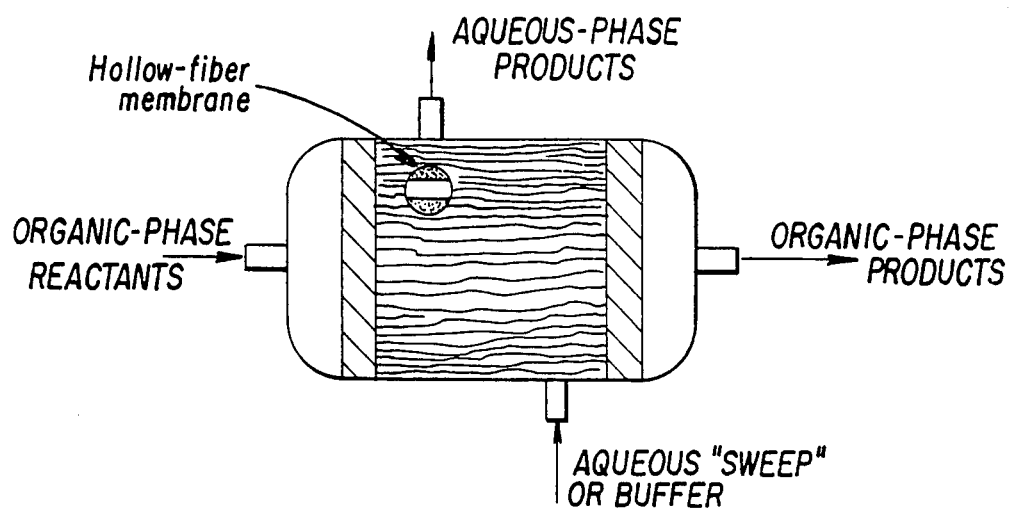
FIG. 5 is a schematic representation of a hollow-fiber multiphase enzyme membrane reactor with organic-phase and aqueous-phase feed and product streams being supplied to and removed from the device.
Figure 6:
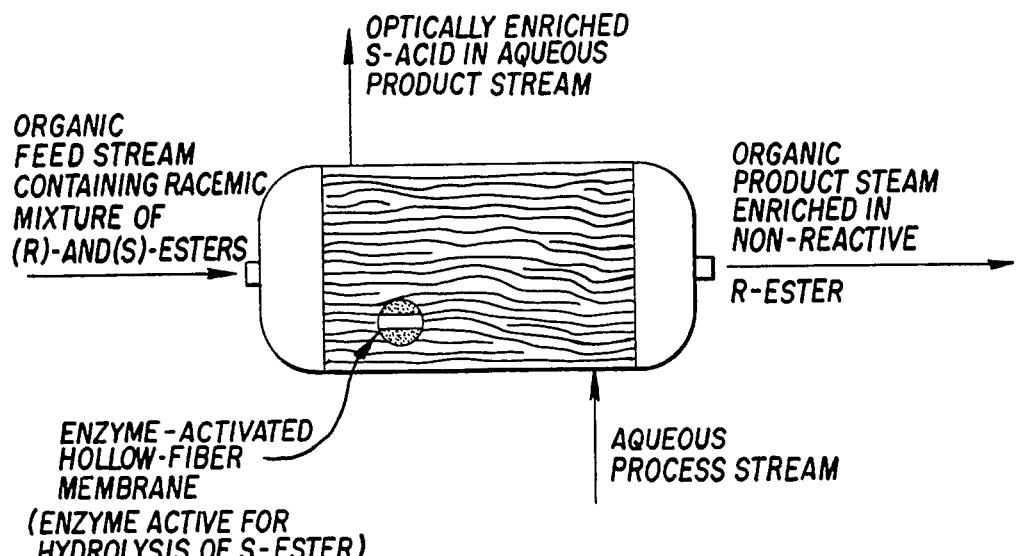
Figure 7:
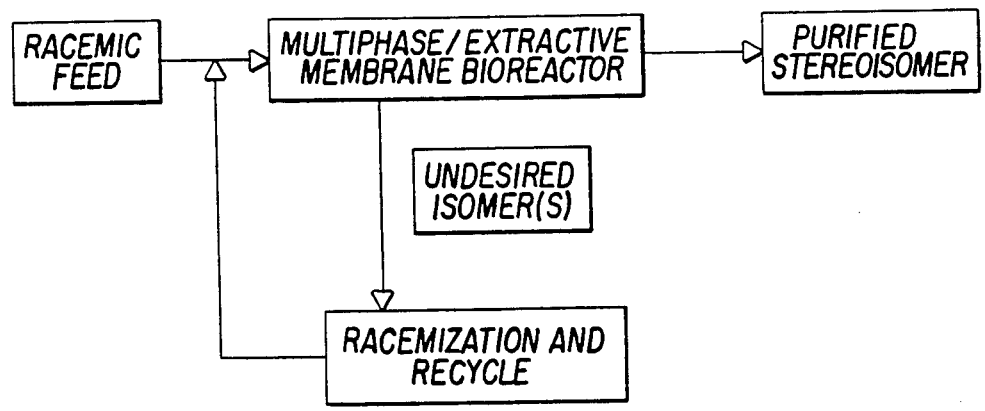
Figure 8:
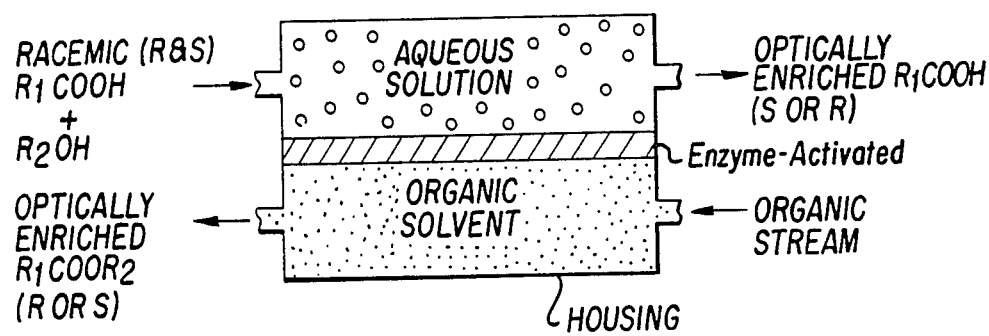
Figure 9:
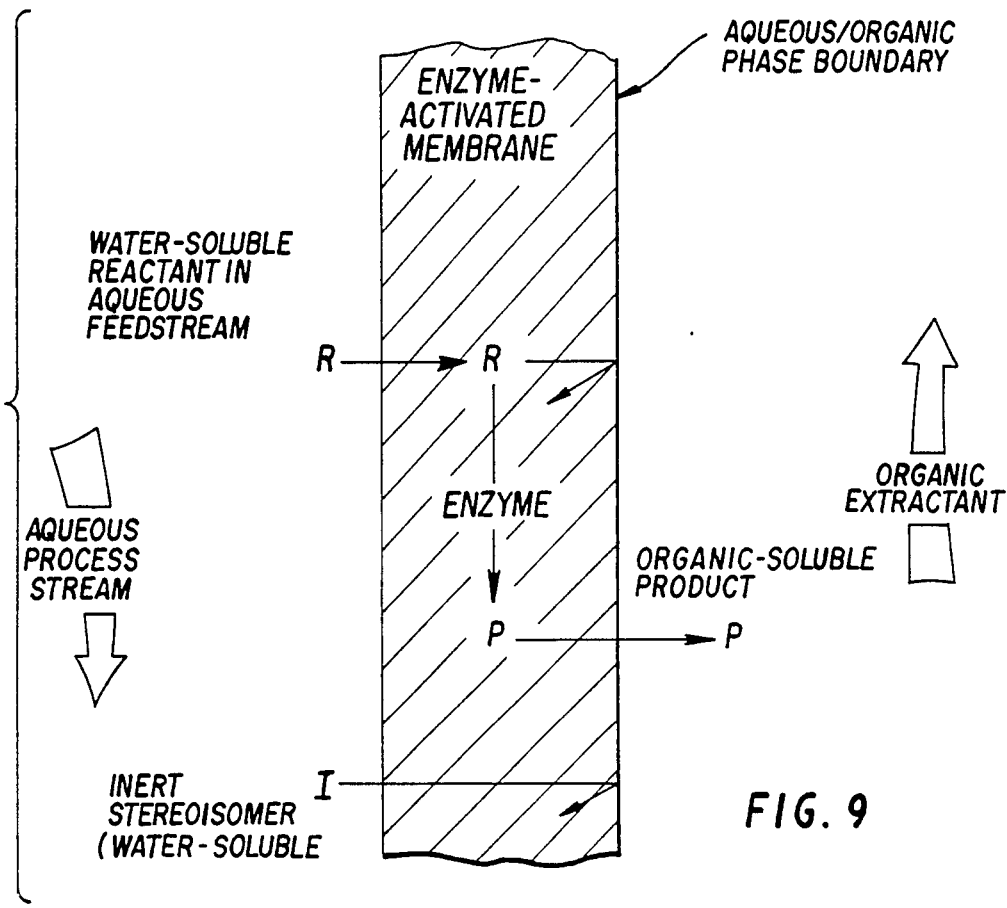

FIG. 6 illustrates how optical resolution of a chiral S-acid is accomplished in the reactor of FIG. 5 by the supply of a racemic mixture of organic-soluble esters in the organic-phase feed stream and by the removal of organic- and aqueous-phase product streams, enriched in the relatively non-reactive R-ester and in the S-acid, respectively, wherein the materials contained in the organic and aqueous streams are optically purified and exhibit opposite stereochemical configurations; and FIG. 7 shows an example of an integrated resolution/racemization/recycle process for the production of a singly optically purified product, wherein the inactive isomers are racemized and recycled internal to the process with the net result that only material of the desired stereochemical configuration is produced;

FIG. 8 is a schematic representation of a method for the resolution of a racemic mixture of organic acids, in which the mixture is fed in an aqueous solution to one side of an enzyme-activated membrane, and one isomeric component of the racemic acid mixture is stereoselectively combined with a water-soluble alcohol in an enzyme-catalyzed esterification reaction, and the optically enriched ester product of reaction is removed by a countercurrent process stream consisting of a water-immiscible organic solvent for the product ester which is fed onto the opposite side of the membrane;

FIG. 9 is a schematic, cross-sectional view of the enzyme-activated membrane in an extractive membrane reactor process, along with the organic and aqueous process streams in contact with it, for the purpose of illustrating the diffusion and reaction fluxes, as well as the phase partitioning behavior, of the various organic- and water-soluble participants in the reaction process.

Figure 10:
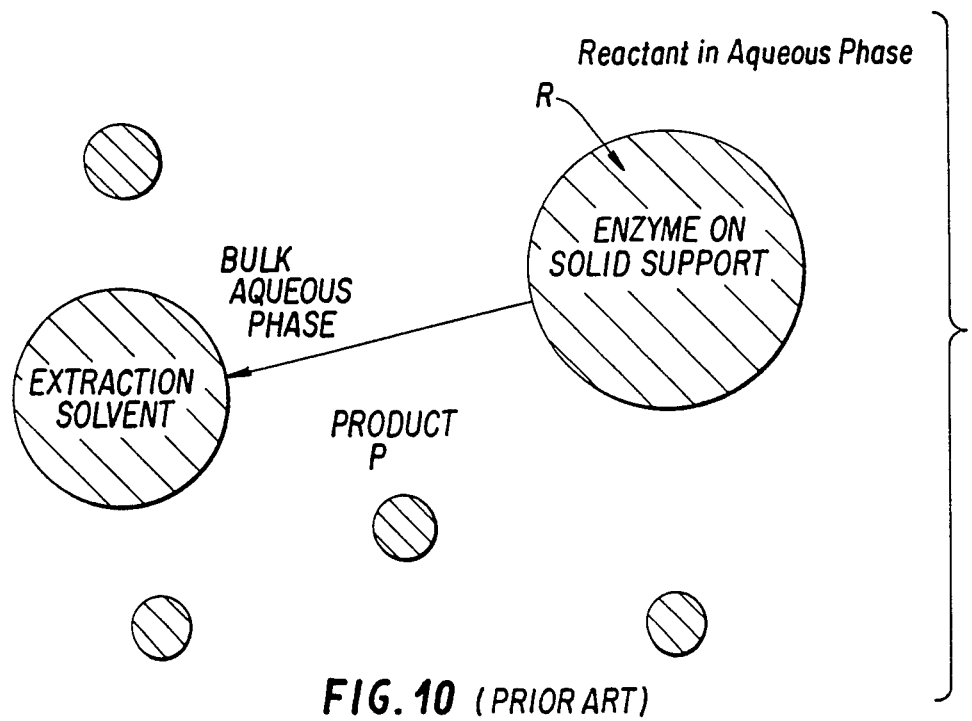
Figure 11:
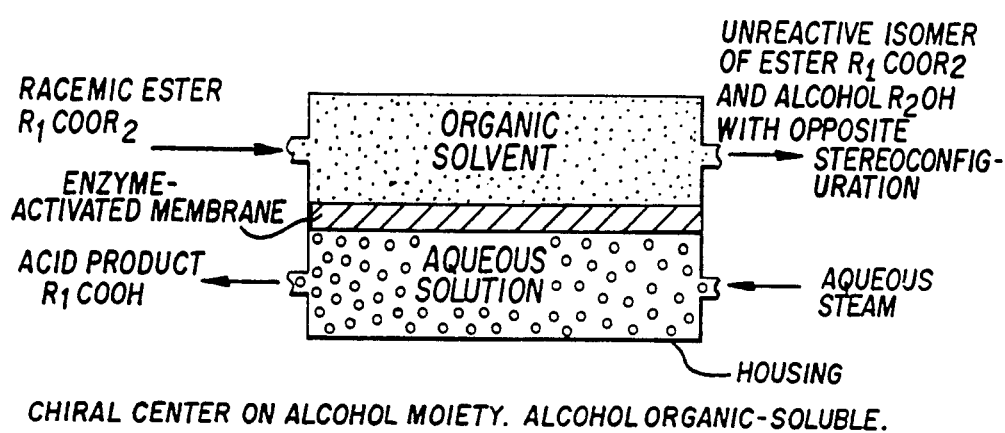
Figure 12:
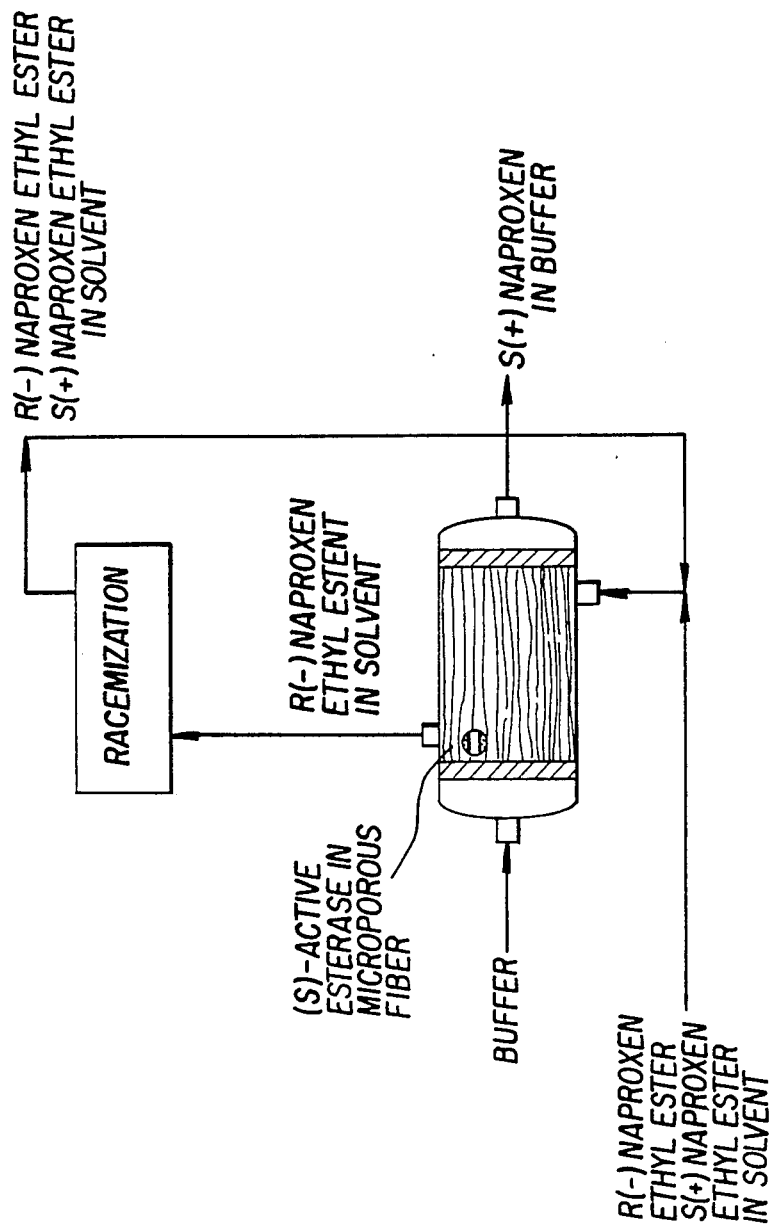
Figure 13:
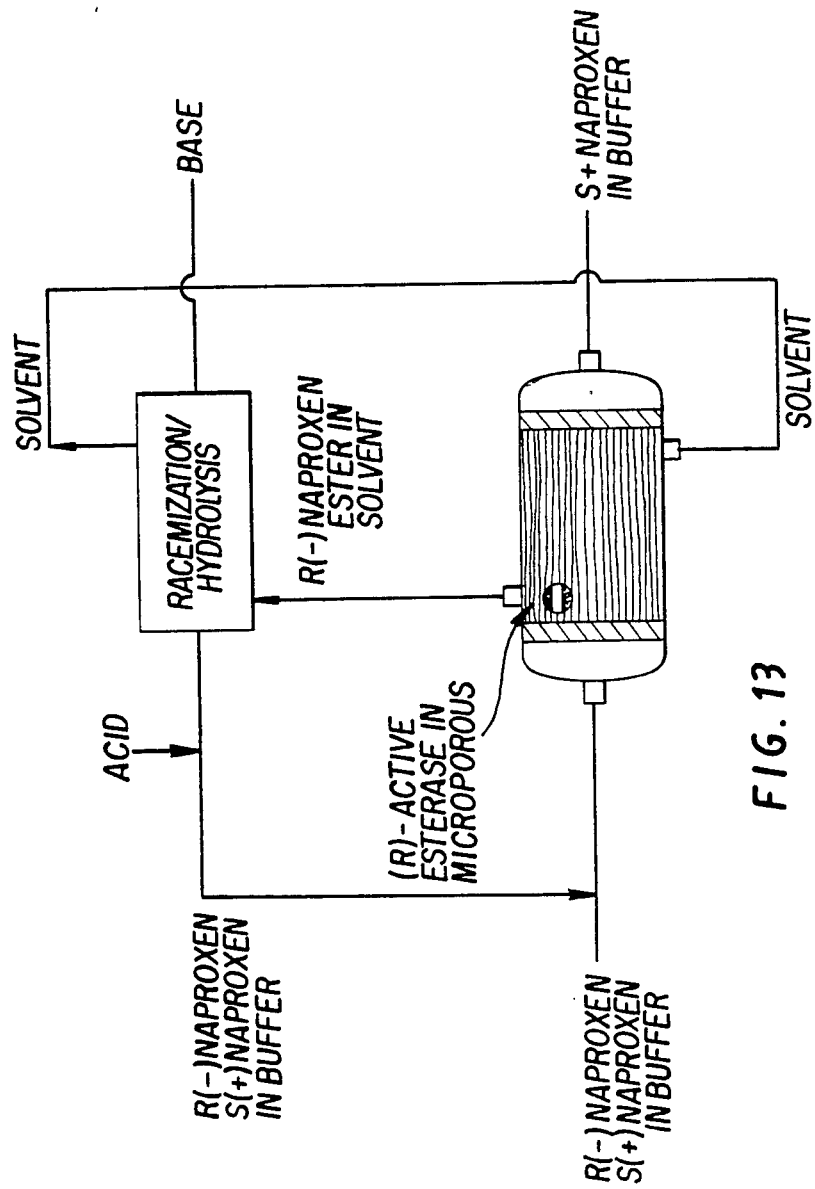
Figure 14:
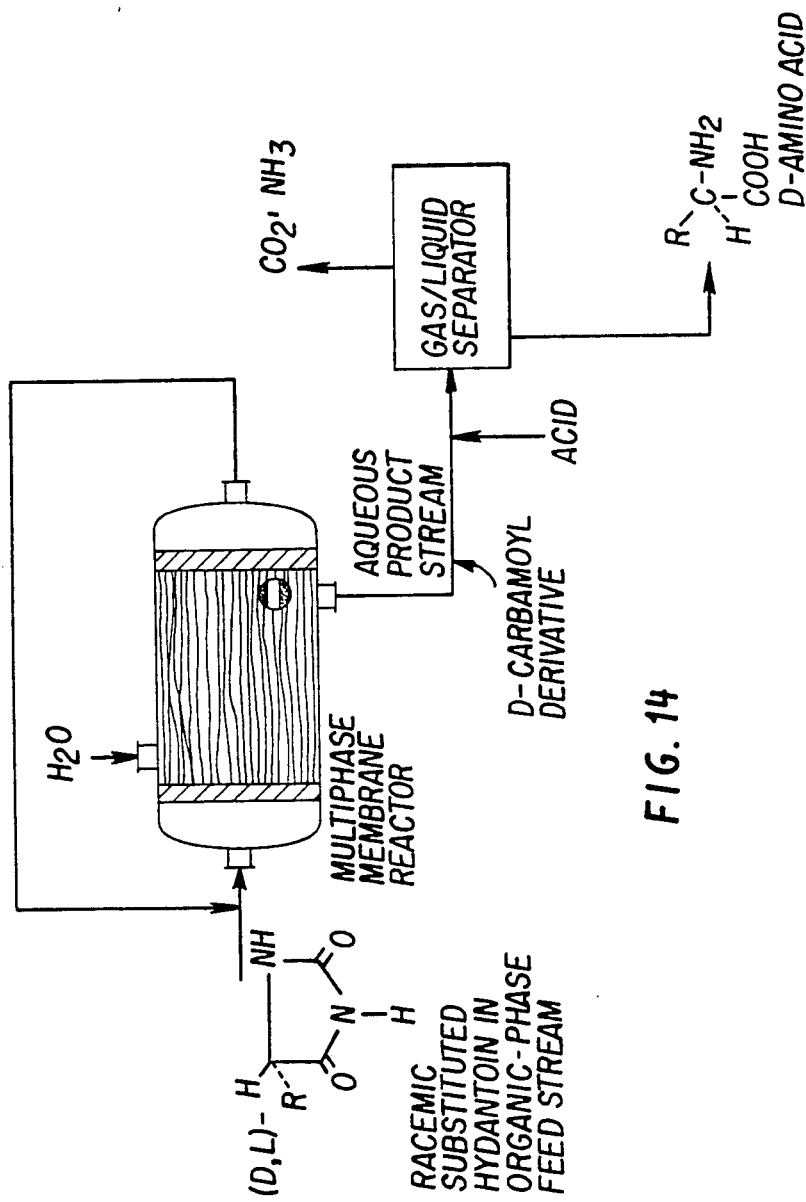
Figure 15:
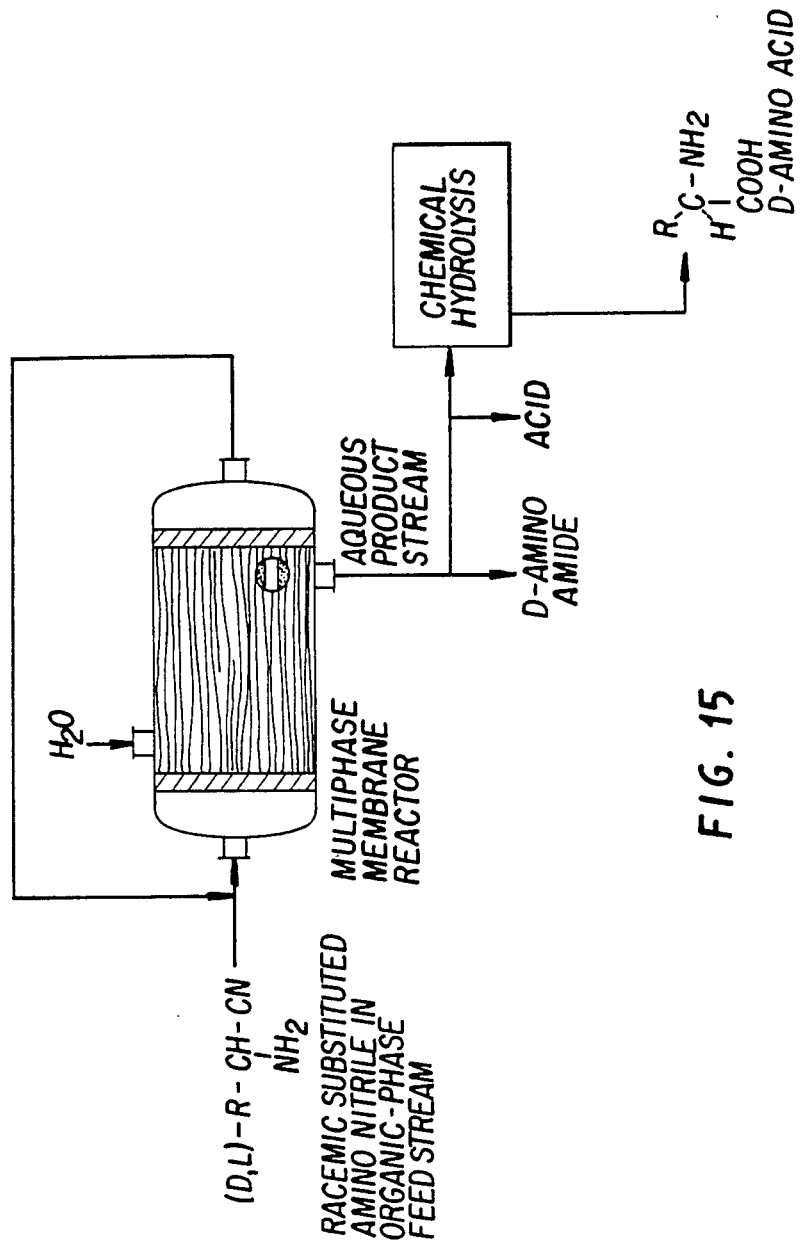
Figure 16:
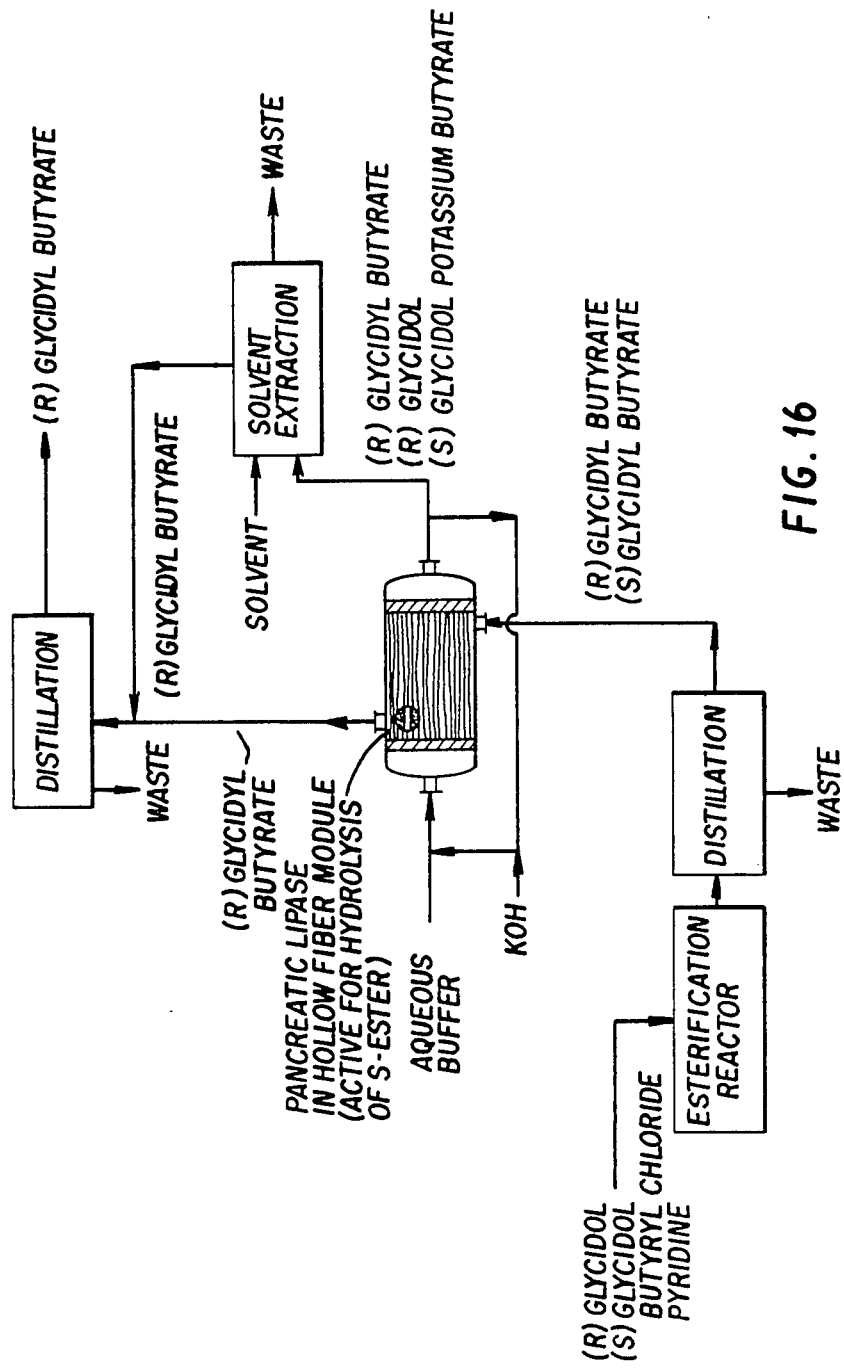

FIG. 10 shows, for purposes of comparison, the disposition of the three-phases in a conventional, dispersed-phase extractive bioreactor operation;

FIG. 11 is a schematic representation of a method for the resolution of a racemic mixture of organic-soluble esters, in which one ester isomer in the racemic mixture fed via an organic-phase process stream onto one side of an enzyme-activated membrane is stereospecifically hydrolyzed by the enzyme to a chiral and organic-soluble alcohol (and the corresponding water-soluble acid), wherein the unreactive ester isomer and the product alcohol isomer exit the membrane reactor via the organic process stream and the acid product exits via the aqueous phase;

FIG. 12 illustrates a multiphase enzyme membrane reactor process for the production of optically purified naproxen utilizing an S-active enzyme, wherein a racemic mixture of an ester derivative of naproxen is fed to the reactor in the form of an organic solvent, with the desired and resolved S-acid product being removed from the reactor via an aqueous buffer stream, and the unreactive R-ester being racemized and recycled to the reactor for subsequent conversion to the desired S-naproxen acid product;

FIG. 13 illustrates an extractive enzyme membrane reactor process for the production of optically purified naproxen utilizing an R-active enzyme, wherein a racemic mixture of naproxen acids is fed to the reactor in the form of an aqueous solution and the undesired R-form of the acid reacts with an alcoholic coreactant (not shown) to produce the organic-soluble R-ester of naproxen, and further with this R-ester being removed from the reactor via an organic solvent stream, subsequently to be racemized and hydrolyzed back to the acid for recycle to the process and ultimate conversion to the desired S-naproxen acid product;

FIG. 14 shows a multiphase enzyme membrane reactor process flowsheet for the production of resolved D-amino acids from racemic, organic-soluble substituted hydantion precursors employing a D-stereoselective hydantoinase enzyme, wherein a water-soluble D-carbamoyl amino acid intermediate product is removed from the membrane reactor via the aqueous process stream, subsequently to be acidified to produce the resolved D-amino acid product, with the unreactive L-form of the organic-soluble hydantoin undergoing spontaneous racemization and eventual enzymatic conversion;

FIG. 15 shows a multiphase enzyme membrane reactor process flowsheet for the production of resolved D-amino amides and D-amino acids from racemic, organic-soluble amino nitrile precursors employing a D-stereoselective nitrilase or nitrile hydratase enzyme, wherein a water-soluble D-amino amide is produced and removed from the membrane reactor via the aqueous process stream, optionally to be converted to the corresponding D-amino acid by acid hydrolysis if desired, with the unreactive L-form of the organic-soluble amino nitrile undergoing spontaneous racemization and eventual enzymatic conversion; and FIG. 16 shows a multiphase enzyme membrane reactor and reactant/product purification process flowsheet for the production of optically resolved R-glycidyl butyrate, wherein a racemic mixture of organic-phase glycidyl butyrate stereoisomers is fed on one surface of a lipase-activated membrane and the organic phase is preferentially depleted in the undesired S-ester and enriched in the desired R-ester.

4.0 DETAILED DESCRIPTION OF THE INVENTION

4.1 Enzymatic Resolution of Racemic Mixtures

Generally stated, this invention provides a method for resolving a racemic mixture comprising:

a. providing in a first fluid a racemic mixture having at least a first and second stereoisomer to one side of an enzyme activated membrane wherein said enzyme which activates said membrane catalyzes the reaction of the first stereoisomer into a chiral product having an altered chemical composition;

b. providing concurrently a second fluid, substantially immiscible in said first fluid, to the opposite side of said enzyme activated membrane, whereby said racemic mixture is resolved with said chiral product of step a principally diffusing into said second fluid from said enzyme activated membrane so that said second fluid predominantly includes said chiral product and said first fluid predominantly includes said second stereoisomer.

This invention further provides a method for resolving a racemic mixture comprising:

a. providing a racemic mixture having at least a first and second stereoisomer in a first fluid to one side of an enzyme activated membrane wherein said enzyme which activates said membrane catalyzes the reaction of the first stereoisomer into a chiral product having an altered chemical composition and a second product and;

b. providing concurrently a second fluid, substantially immiscible in said first fluid, to the opposite side of said enzyme activated membrane, said chiral product of step a principally diffusing into said first fluid from said enzyme activated membrane and said second product principally diffusing into said second fluid.

whereby said racemic mixture is resolved with said first fluid containing said second stereoisomer and said chemically distinct chiral product.

In addition, this invention provides a method for producing a chiral product from an achiral precursor comprising:

a. providing a first fluid containing an achiral precursor to one side of an enzyme activated membrane wherein said enzyme which activates said membrane catalyzes the reaction of said achiral precursor into a chiral product;

b. providing concurrently a second fluid substantially immiscible in said first fluid, to the opposite side of said enzyme activated membrane, said chiral product of step a principally diffusing into said second fluid from said enzyme activated membrane, whereby said second fluid contains said chiral product.

More specifically, this invention concerns the use of the above processes in multiphase and extractive enzyme membrane reactors for the stereoselective synthesis or resolution of racemic mixtures of chiral organic acids, alcohols, amines, esters, amides, nitriles, hydantoins, and other chiral compounds in which the membrane supports, entraps, or otherwise contains an enzyme capable of stereoselectively catalyzing a reaction to convert one isomer or achiral precursor to a chemically distinct optically active compound. Enzymes are well suited to the role of stereoselective catalysis inasmuch as they contain asymmetric, catalytically active sites in which the molecule being synthesized or undergoing resolution may bind. Because these enzyme active sites are themselves asymmetric, they permit two enantiomers of a given racemic substrate to be acted upon differentially, and they permit chiral products to be formed from achiral precursors.

For example, many enzymes exist that effectively catalyze the hydrolysis or condensation of ester and amide chemical functional groups. Many of these enzymes, but not all of them, belong to either one of two main classes of enzymes known as hydrolases or lyases, as defined in the Recommendations of the Commission on Biochemical Nomenclature, Elsevier, Amsterdam, The Nomenclature and Classification of Enzymes (1972) p.17–22. The term E.C. followed by a series of numbers as used herein, provides the identification of an enzyme pursuant to the Commission Recommendations.

Specific examples of such enzymes include but are not limited to trypsin, chymotrypsin, thermolysin, rennin, pepsin, papain, carboxy peptidases, amino peptidases, penicillin and cephalosporin acylase, acetyl cholinesterase, cholesterol esterase, and mammalian pancreatic lipases and peptidases.

For example, a generally preferred source of lipase (E.C. 3.1.1.3) is *Candida cylindracea* (*C. rugosa*), and typically preferred esterases include chymotrypsin (E.C. 3.4.21.1) and y (E.C. 3.4.21.14) because of their ready availability, high stereoselectivity, and broad substrate range. Other microbial sources of lipases include, but are not limited to, *Pseudomonas aeruginosa, Pseudomonas flourecens, Rhizopus arrhizus, Rhizopus delemar, Rhizopus niveus, Rhizopus oryzae, Rhizopus japonicus, Chromobacterium viscosum, Geotrichium candidum, Aspergillus niger, Aspergillus sojae, Aspergillus oryzae, Mucor miehei, Penicillium roqueforti, Pencillium cyclopium, Achromobacter lipolyticum, Alcaligenes* sp., *Thermomyces lanuginosus, Pycomyces nitens, Arthrobacter* sp., *Fusarium oxysporium, Candida lipolytica,* and *Humicola lanuginosa.* Pancreatic lipases from various mammalian species and lipase derived from wheat germ may also be employed. Other esterases derived from mammalian sources include, but are not limited to, carboxyl esterase (E.C. 3.1.1.1.), carboxypeptidase A (E.C. 3.4.17.1), acetyl cholinesterase (E.C. 3.1.1.7), pepsin (E.C. 3.4.23.1) and trypsin (E.C. 3.4.21.4). Other microbial sources include *Bacillus thermoproteolyticus* (for thermolysin), *Bacillus amyloliquefaciens* and *Streptomyces griseus* as well as papain (E.C. 3.4.22.2) derived from *Papaya latex*.

Depending upon the source, lipases and esterases have a working pH range from about 2 to about 10, with their optimum pH generally falling between 5.0 and 8.5. Temperature range for most enzymes encompass 15° to 70° C., with the enzymes usually performing most effectively in the range from 20°–45° C.

As noted above, this invention also concerns the use of membrane bioreactors for the resolution of racemic mixtures of chiral organic nitriles. Enzymes suitable for this purpose would catalyze the hydrolysis of a nitrile function, to either the corresponding amide, or directly to the corresponding carboxylic acid. Such enzymes could be from, but are not limited to, the main class of enzymes known as hydrolases. Currently, enzymes which transform a nitrile to an amide are called "nitrile hydratases," and enzymes transforming a nitrile directly to a carboxylic acid are called "nitrilases." These names have no official status, but are widely used in the current literature. "Nitrile hydratase" has been assigned the Chemical Abstracts Registry Number [82391-37-5], and "nitrilase" has been assigned Registry Number [9024-90-2]. It should be recognized that it is also included within the scope of this invention to use "nitrile hydratase" activity, together with "amidase" activity, to transform a nitrile to its corresponding carboxylic acid.

Enzymes used in this invention to transform nitrile functional groups, are generally, but not exclusively, found in micro-organisms. Micro-organisms in which "nitrile hydratase" activity has been found are contained in, but not limited to, the following genera: Aeromonas, Arthrobacter, Brevibacterium, and Pseudomonas. Micro-organisms in which "nitrilase" activity has been found are contained in, but not limited to, the following genera: Arthrobacter, Aspergillus, Bacillus, Bacteridium, Corynebacterium, Fusarium, Klebsiella, Micrococcus, and Nocardia. One or both of these two enzymatic activities have also been observed in the genera: Agrobacterium, Achromobacter, Rhodotorulla, Paracoccus, Acetobacter, and Escherichia.

Stereospecific hydrolyses of racemic amino acid hydantoins to yield optically active carbamoyl amino acids are catalyzed by enzymes belonging to the category of dihydropyrimidinase (E.C. 3.5.2.2.), also known more informally as "hydantoinases." Dihydropyrimidinase can be obtained from mammalian sources, including, but not limited to, bovine liver or from microbial sources including bacteria, actinomycetes, molds, yeasts and deuteromycetes. Examples of bacterial enzyme sources are Achromobacter, Aerobacter, Aeromonas, Agrobacterium, Alcaligenes, Arthrobacter, Bacillus, Brevibacterium, Corynebacterium, Enterobacter, Erwinia, Escherichia, Klebsiella, Microbacterium, Micrococcus, Protaminobacter, Proteus, Pseudomonas, Sarcina, Serratia and Xanthomonas. Examples of actinomycetes are Actinomyces, Actinoplanes, Mycobacterium, Nocardia and Streptomyces. Molds include Aspergillus, Paecilomyces and Penicillium. Yeasts include Candida, *Rhodotorula pichia* and Torulopsis. Although the broad working ranges of pH and temperature over which the hydantoinases are active correspond roughly to those given above for other hydrolytic enzymes, their optimum pH range is typically somewhat higher, about pH 7 to 9.

In addition to isolated and purified enzymes, it should be noted that the processes of the present invention may also be carried out employing relatively impure and/or heterogeneous enzyme preparations, such as those derived from cell extracts, cell lysates, and partially purified enzyme isolates, albeit at some reduction in the enzymatic activity associated with the enzyme-activated membrane. Indeed, enzymes contained within whole cells, whether viable or not, may also be used in the practice of this invention, and accordingly it is intended that the term "enzyme" as used herein is meant to broadly include biocatalytic enzymes in all of these forms.

Types of enzymatic reactions useful in the practice of the present reaction include, but are not limited to, the following categories:

hydrolysis of esters to form acids and alcohols;
formation of esters (i.e., esterifications) from acids and alcohols;
transesterification, i.e., reaction of an ester with an alcohol or acid to form a different ester and a different alcohol or acid;
transaminations (e.g., reaction between an alpha-keto acid and an amino acid);
hydrolysis of amides (including peptide bonds and N-acyl compounds) to form acids and amines;
formation of amides (including peptides) from acids and amines (or amino acids);
hydrolysis of amino acid hydantoins to yield carbamoyl amino acids and amino acids; and
hydrolysis of nitriles to form the corresponding amides and carboxylic acids (and in particular, hydrolysis of amino nitriles to amino amides and amino acids).

Particular chiral compounds and precursors or derivatives thereof which, by the process of the present invention, it is desired to prepare either by chiral (i.e., asymmetric) enzymatic synthesis and/or enzymatic resolution of a racemic mixture of chemically synthesized enantiomers include, but are not limited to, the following: naproxen or 2-(6-methoxy-2-naphthyl)propionic acid; ibuprofen or 2-(4-isobutylphenyl)propionic acid; ketoprofen or 2-(3-benzoylphenyl)propionic acid; flurbiprofen or 2-(2-fluoro-4-biphenylyl)propionic acid; S-benzoyl-beta-mercapto isobutyric acid; 2-bromopropionic acid and esters thereof; 2-chloropropionic acid and esters thereof; parahydroxyphenylglycine and phenylglycine; 2-amino-2,3-dimethylbutyric acid, and 2-amino-2,3-dimethylbutyramide; amino acids including L-dopa and methyl dopa; beta-mercaptoisobutyric acid; glycidol and glycidyl butyrate; lactic acid; carnitine; tartaric acid; 2-bromophenylbutyric acid ethyl ester; peptides including "aspartame" and "alitame"; aryloxypropanolamines including propranolol and 1-acetoxy-2-aryloxy-propionitriles including 1-acetoxy-2-alphanaphthyloxypropionitrile; alpha-aryloxypropionic acids and ester derivatives thereof including 2-phenoxypropionic acid, butyl 2-[4-[[5-(trifluoromethyl)-2-pyridinyl]oxy]phenoxy]-propanoate, methyl 2-[4-[[5-(trifluoromethyl)-2-pyridinyl]oxy]phenoxy]propanoate, methyl 2-[4-(2,4-dichlorophenoxy)phenoxy] propionate and methyl 2-(4-hydroxyphenoxy)propionate; 5-substituted hydantoins and thiohydantoins; pyrethroid insecticides including cypermethrin and fluvalinate; 2-(p-chlorophenoxy)-propionic acid; cyanohydrins including alpha-cyano-3-phenoxybenzyl alcohol; 4-hydroxy-3-methyl-2,2'-propynyl-2-cyclopentenone; 4-amino-3-hydroxybutyric acid; 1-methoxy-2-hydroxypropane; 4-ethyl-2-piperidinecarboxylic acid; N-[2-hydroxy-2-(3-formamido-4-hydroxyphenyl)]-1-phenyl-3-aminobutane; N-(1-carboxyethyl-3-phenylpropyl)-2-aminopropionic acid; 2-indolenecarboxylic acid; 2-amino-2-methyl-3-(3,4dihydroxyphenyl)propionitrile and 2-amino-2-methyl-3-(3-methoxy-4-hydroxyphenyl)propionitrile; methyl-2-amino-3-hydroxy-3-(4-nitrophenyl)propionate; 2-[(1-carbamoyl-1,2-dimethylpropyl)-carbamoyl]-nicotinic acid and 2-[(1-cyano-1,2-dimethylpropyl)-carbamoyl]-nicotinic acid; and N-(3-phenyl-1-carboxypropyl)-2-aminopropionic acid and esters thereof.

The chemical nature (e.g., identity of functional groups) of many particular reactants and products will be evident from the above partial lists of reaction categories, reactions, and products. It will be appreciated from these lists that a majority of these reactions falls into one of two classes: either (i) substantially water-insoluble, organic-soluble reactants are converted to water-soluble products, or (ii) water-soluble, substantially organic-insoluble reactants are converted to organic-soluble product species. Such types of reactions are particularly suited for conduct in multiphase and extractive membrane reactor processes, respectively. As an example of the former category of reactions, esters that are sparingly soluble in water may be efficiently hydrolyzed to appreciably water-soluble acids in multiphase membrane reactor processes. The corresponding alcoholic coproduct may be preferentially soluble in either the aqueous or organic phase. Conversely, acids that are highly water soluble but not appreciably soluble in organic solvents by virtue of their electrical charge may be efficiently converted into esters in extractive membrane reactor processes, wherein the esters do, in fact, exhibit significant solubility in organic solvents which facilitates their removal from the reaction zone by virtue of their selective extraction into a solvent. In this case, the alcoholic coreactant may be supplied to the extractive membrane reactor via either the aqueous or organic process stream, depending on the solubility characteristics of the alcohol.

In multiphase and extractive membrane reactor processes, the stereoselective enzymatic reaction may be conducted either using the racemic form of the desired compound itself as the reactant mixture or using a simple chemical derivative thereof as the reactant mixture. In particular, the enzymatic resolution of chiral acids or chiral alcohols can be effected in a number of ways in membrane reactors; two preferred membrane reactor processes involve (i) the stereoselective enzymatic hydrolysis of a racemic mixture of ester derivatives of the desired product in a multiphase membrane reactor, and (ii) the stereo-selective enzymatic esterification of the chiral acid or alcohol in an extractive membrane reactor. In both cases, the selection of the acid or alcohol moiety used to form the ester derivative with the desired chiral alcohol or chiral acid is important to efficient operation of the membrane reactor processes. For example, these compounds can be selected to manipulate the water-solubility of the ester derivatives as well as to maximize enzyme activity and stereoselectivity towards the derivatives. Alcohols useful in esterifying chiral acids such as naproxen and ibuprofen include, but are not limited to, compounds represented by the formula $RCH_2OH$, where R represents hydrogen, an alkyl group containing from 1 to 18 carbons, $-CN$, $-CCl_3$, $-CH_2Cl$, $-CHNO_2CH_3$, $-C\equiv CH$, $-CH=CH_2$, $-COCH_3$, $-COO-$alk, or $CH_2O-$alk where the alkyl group ,alk, contains from 1 to 4 carbons. Acids for esterifying chiral alcohols such as glycidol and menthol include, but are not limited to, compounds represented by RCOOH, where R represents an alkyl group containing from 1 to 18 carbons or $-CH_2CH_2COOH$. Also useful in this regard are the phosphate esters of chiral alcohols.

For example, preferred chiral esters, racemic mixtures of which may be resolved by the process of this invention include glycidyl butyrate and methyl 2-(4-hydroxyphenoxy)propionate. It is also foreseeable that the present invention will be used to resolve racemic mixtures of chiral esters selected from the group consisting of 2-bromophenylbutyric acid ethyl ester, S-benzoyl-beta-mercaptoisobutyric acid (a thiol ester), the butyl and methyl esters of 2-[4-[[5-(trifluoromethyl)-2-pyridinyl]oxy]phenoxy]propionic acid, methyl 2-[4-(2,4-dichlorophenoxy)phenoxy]propionate, alpha-cyano ester pyrethroids including cypermethrin and fluvalinate, methyl 2-amino-3-hydroxy-3-(4-nitrophenyl)propionate, and 1-acetoxy-2-aryloxypropionitriles including 1-acetoxy-2-alpha-napthyloxypropionitrile.

Preferred chiral acids, racemic mixtures of which may be resolved by the process of this invention include naproxen, ibuprofen, ketoprofen, and fluriprofen; S-benzoyl-beta-mercaptoisobutyric acid; 2-halopropionic acids including 2-chloropropionic and 2-bromopropionic acids; amino acids including dopa, phenylglycine, and parahydroxyphenylglycine; alpha-aryloxypropionic acids including 2-phenoxypropionic acid, 2-(p-chlorophenoxy)propionic acid, and 2-(4-hydroxyphenoxy)propionic acid. It is also foreseeable that the process of the present invention may be used to resolve racemic mixtures of chiral acids selected from the group consisting of beta-mercaptoisobutyric acid; methyl dopa; peptides including aspartame and alitame; 2-acetylamino-2,3-dimethylbutyric acid; carnitine; lactic and tartaric acids; 2-bromophenylbutyric acid; 2-[4-[[5-(trifluoromethyl)-2-pyridinyl]oxy]phenoxy]propionic acid;2-[4-(2,4-dichlorophenoxy)phenoxy]propionic acid; chrysanthemic acid and derivatives thereof; 4-amino-3-hydroxybutyric acid; 4-ethyl-2-piperidine-carboxylic acid; N-(1-carboxyethyl-3-phenylpropyl)-2-aminopropionic acid; 2-indolenecarboxylic acid; 2-amino-3-hydroxy-3-(4-nitrophenyl)propionic acid; and N-(3-phenyl-1-carboxypropyl)-2-aminopropionic acid.

Such chiral acids may be resolved directly by feeding racemic mixtures thereof directly to a multiphase or extractive membrane reactor process. Alternatively, racemic mixtures of ester or amide derivatives of chiral acids may first be prepared by reacting these racemic acids with alcohols or amines, respectively, and then feeding said racemic mixture of ester or amide deivatives to a membrane reactor process to effect the resolution of the original racemic acid mixture in an indirect manner.

In another preferred embodiment of this invention, racemic mixtures of chiral alcohols are resolved wherein the chiral alcohol is glycidol, carnitine, cyanohydrin alcohols including alpha-cyano-3-phenoxybenzaldehyde, or 4-hydroxy-3-methyl-2,2,-propynyl-2-cyclopentenone. It is also foreseeable in the practice of this invention that the chiral alcohol could be one selected from the group consisting of aryloxypropanolamines including propranolol; amino acids containing side-chain hydroxyl groups including para-hydroxyphenylglycine; beta-mercaptoisobutric acid (strictly speaking, a thiol); 4-amino-3-hydroxybutyric acid; 1-methoxy-2-hydroxypropane; N-[2-hydroxy-2-(3-formamido- 4-hydroxyphenyl)]-1-phenyl-3-aminobutane; 2-amino-2-methyl-3-(3,4-dihydroxyphenyl)propionitrile and 2-amino-2-methyl-3-(3-methoxy-4-hydroxyphenyl)-propionitrile; and 2-amino-3-hydroxy-3-(4-nitrophenyl)propionic acid and the methyl ester thereof.

On the one hand, racemic mixtures of such chiral alcohols may be resolved by feeding the racemic alcohol mixture directly to the enzyme membrane reactor process of this invention. One the other hand, a racemic mixture of chiral ester derivatives may first be prepared by reacting the racemic alcohol mixture with an acid and then feeding this racemic ester mixtureto a membrane reactor to effect the resolution of the racemic alcohol mixture in an indirect manner.

Preferred chiral amides, racemic mixtures of which may be fed to and resolved by the membrane reactor process described herein include 2-amino-2,3-dimethylbutyramide, 2-acetylamino-2,3-dimethylbutyric acid, and peptides including aspartame and alitame. It is also foreseeable that the present invention could be applied to the resolution of racemic amino acids containing side-chain amide groups and to 2-[(1-carbamoyl-1,2-dimethylpropyl)-carbamoyl]-nicotinic acid.

A preferred chiral amine, the racemic mixture of which may be supplied to and resolved in the present membrane reactor process, is phenylglycine, where the stereoselective enzymatic reaction involves the alpha-amino group. It is also foreseeable that the present invention may be applied to the resolution of racemic amines selected from the group consisting of 2-amino-2,3-dimethylbutyronitrile; 2-amino-2,3-dimethylbutyramide; amino acids including dopa and para-hydroxyphenylglycine; peptides including aspartame and alitame; aryloxypropanolamines including propranolol; 4-amino-3-hydroxybutyric acid; 4-ethyl-2-piperdinecarboxylic acid; N-(1-carboxyethyl-3-phenylpropyl)-2-aminopropionic acid; 2-amino-2-methyl-3-(3,4-dihydroxyphenyl)propionitrile and 2-amino-2-methyl-3-(3-methoxy-4-hydroxyphenyl)propronitrile; and 2-amino-3-hydroxy-3-(4-nitrophenyl)propionic acid and the methyl ester thereof.

On the one hand, racemic mixtures of such chiral amines may be resolved by feeding the racemic amine mixture directly to the membrane reactor process. Alternatively, a racemic mixture of chiral amide derivatives may first be prepared by reacting the racemic amine mixture with an acid and then subjecting the resulting racemic amide mixture to resolution in the enzyme membrane reactor process. As a result, the original racemic amine mixture is resolved in an indirect fashion.

Finally, it is also foreseeable that the present invention will be used in the resolution of racemic mixtures of various chiral nitrile compunds selected from the group consisting of 2-amino-2,3-dimethylbutyronitrile; 1-acetoxy-2-aryloxypropionitriles including 1-acetoxy-2-alpha-naphthyloxypropionitrile; 2-amino-2-methyl-3-(3,4-dihydroxyphenyl)propionitrile and 2-amino-2-methyl-3-(3-methoxy-4-hydroxyphenyl)propionitrile; and 2-[(1-cyano-1,2dimethylpropyl)carbamoyl]-nicotinic acid.

The difference in solubilities of key reactants and products in multiphase membrane reactor schemes will be seen typically to result from the conversion of a relatively non-polar and/or uncharged functional group (e.g., an ester or amide linkage) to a more polar and/or charged functional group (e.g., a carboxylic acid), whereas just the opposite is generally true (i.e., polar/charged functional groups are transformed to relatively apolar/uncharged groups) in extractive membrane reactor processes.

Typically, but not necessarily, the partition coefficients, i.e., the ratios of organic-phase to aqueous-phase species concentrations at phase equilibrium, or aqueous-to-organic phase concentration ratios, will exceed two for key reactants and products, and preferably the distribution ratios of the key components will exceed about 10 for optimum performance of multiphase and extractive membrane reactor processes. Under ideal circumstances, partition coefficient ratios can exceed 100 or more, leading to very efficient reactor operation and reactant/product stereoisomer separations, but such extreme solubility differences are not required in order to practice the invention.

Absolute solubilities of reactants and products in the aqueous and organic-based phases are much less important to the practice of the present invention, with both the multiphase and extractive membrane reactor process embodiments having been operated successfully under conditions where the concentration of either reactant or product in one or more of the phases was of order micromoles per liter or lower. At the opposite extreme, water-insoluble reactants that are liquids at enzymatic reaction temperatures can be fed directly as neat liquids, at very high concentrations, to multiphase membrane reactor processes. Alternatively, where the sparingly water-soluble reactant is a solid or very viscous liquid, it is convenient to dissolve it in an organic solvent such that the resulting solution is immiscible with water. Solvents that have been found useful for this purpose include but are not limited to aliphatic and aromatic hydrocarbons such as hexane and toluene; chlorinated solvents such as methylene chloride and chloroform; water-immiscible alcohols including amyl alcohol, octanol, and decanol; esters including amyl acetate; and ketones such as methyl isobutyl ketone. In choosing a solvent for use in a multiphase or extractive membrane reactor process, important considerations include its compatibility with the membrane material and enzyme, as well as its toxicity, viscosity, solubility and miscibility characteristics, and its ability to be readily separated from other reaction components.

4.2 Membrane Structure and Enzyme Containment

Enzyme-activated membranes suitable for the practice of this invention will be chosen with several considerations in mind, namely, chemistry, morphology, and mode of enzyme activation. With regard to the first of these, the membrane material must be such that it will not be deleteriously effected (e.g., swollen or chemically attacked) by any of the ingredients in the reaction system and, in particular, by organic reactants, products, and/or solvents. Although membranes comprised of inorganic materials (e.g., ceramics) can be used in the practice of this invention, polymeric membranes represent a preferred embodiment. In particular, membranes fashioned from solvent-resistant polymers are well suited to the present process. Typical polymeric materials that can be fabricated into suitable membranes for the practice of this invention include but are not limited to regenerated cellulose, the esters of cellulose (and particularly preferred the partial acetate and nitrate esters), polyacrylonitrile and copolymers thereof (especially the hydrophilic ones including but not limited to copolymers incorporating acrylamide, acrylate, and/or methacrylate functionalities), polyurethane-containing copolymers, the polyarylsulfones and polyarylethersulfones (including polysulfone, polyethersulfone, and blends thereof with such hydrophilic copolymers as polyethyleneoxide, polyhydroxyethers, polyethyleneglycol, polyvinylalcohol, polycaprolactone, and polyepihalogenohydrins), polyvinylidene fluoride, polytetrafluoroethylene, polyvinylalcohol, aliphatic and aromatic polyamides, polyimides, polyetherimides, polyesters, polycarbonates, polyolefins such as polypropylene and polyvinylchloride, polybenzimidazole, and polybenzimidazolone.

The enzyme component of the enzyme-activated membrane will typically function most effectively in an environment that is predominantly aqueous, and for this reason it is preferred that the membrane be water-wet or hydrophilic. Certain of the above membrane polymers are intrinsically hydrophilic (e.g., the cellulosics, many polyacrylonitrile copolymers, and the polyamides). However, even those which are not intrinsically hydrophilic may be rendered suitable for the practice of this invention by an appropriate chemical or physical surface treatment (e.g., by derivatization or attachment of hydrophilic functional groups or simply by contact with an appropriate surfactant), by coating the pore wall surfaces of hydrophobic polymers with hydrophilic materials, or simply by filling the pore volume of an asymmetric, microporous membrane with hydrophilic enzyme in the form of a high-water-content gel.

Membranes suitable for use as enzyme supports can exhibit one of several morphologies. In particular, they may be microporous membranes of the type generally employed in microfiltration processes, wherein the pore sizes will typically range from a few hundredths of micron to several microns, and pore void volumes range from a few percent to 90% and greater. Such microporous membranes may be isotropic (i.e., with no significant variation in pore size from one external surface to the other), or they may exhibit some degree of anisotropy. Ultrafiltration membranes are also useful in the practice of the present invention. They are typicaly highly asymmetric, and characterized by a very thin skin with effective pore sizes in the range of approximately from 1 to 20 nm residing atop a much thicker but more highly porous substrate region comprised of much larger pores. Additionally, gel-type dialysis membranes (e.g., regenerated cellulose membranes of the type used in hemodialysis) may also be employed, particularly where the enzyme is located at the surface of the membrane. Such membranes may be surface-activated either by covalent attachment of the enzyme to an exterior surface or by formation of a dynamic enzyme gel-polarized "secondary membrane" layer at one surface.

In a preferred embodiment, the membrane is largely microporous, characterized by a relatively thick, high-void-volume, finely porous spongy substrate region, but it possesses an ultrafiltration-type skin at one external surface. Such membrane morphologies offer high enzyme loadings and facilitate periodic enzyme replacement. The use of skinned microfiltration membranes with this preferred morphology is described below in connection with modes of enzyme activation.

The geometry of the membrane employed in the practice of this invention is a secondary consideration, and membranes in the forms of flat sheets, tubes preferably of large-diameter, and hollow fibers of various diameters are all useful. Since it is essential that the membrane module have two inlet ports and two outlet ports, plate-and-frame or cassette-type housings are preferred for packaging flat-sheet membrane over spiral-wound cartridges, whereas tubular and hollow-fiber membranes are efficiently packaged in cylindrical multitube or multifiber membrane modules, the construction of which resembles that of a shell-and-tube exchanger. Membranes in the form of hollow-fiber modules permit large areas of membrane to be packaged tightly and economically.

By virtue of the containment, entrapment, or immobilization of enzyme within the membrane phase, any leakage of enzyme out of the membrane and into either the aqueous or organic process streams may be substantially prevented. Suitable means of enzyme incorporation include but are not limited to containment within the pore spaces of asymmetric (i.e., skinned) and microporous membrane structures, adsorption on membrane pore wall surfaces, encapsulation or entrapment in polymeric gels within membrane pores, covalent coupling to membrane pore walls, and crosslinking of enzyme, either within the pore spaces or adsorbed on membrane pore wall surfaces.

More particularly, a number of alternatives exist for the activation of membranes with enzymes. The most straightforward approach involves covalently linking the enzyme to the exterior or interior (i.e., pore wall) surfaces of membranes via any of a number of conventional enzyme immobilization chemistries developed for attaching biocatalysts to non-membrane supports. [See: Zaborsky, O. R., *Immobilized Enzymes*, CRC Press, Cleveland, OH (1973); Weetal, H. H., *Immobilized Enzymes, Antigens, Antibodies, and Peptides: Enzymology*, Vol. 1, Marcel Dekker, N.Y. (1975); Emery, A. et al., Biotechnol. Bioeng., 16:1359 (1974)]. Enzymes may also be crosslinked in porous membranes [Thomas, D. and S. R. Caplan, pps. 351–398 in *Membrane Separation Processes*, P. Meares, ed., Elsevier, Amsterdam (1976)], entrapped in membrane gels [Blaedel, W. J. et al., Anal. Chem., 44:2030 (1972)], encapsulated, or adsorbed on or within membranes via ion-exchange or other specific or non-specific protein-surface interactions. It is also forseeable that in the practice of this invention it will prove effectie in some cases to combine the above techniques. For instance, enzyme may first be adsorbed on membrane exterior or pore wall surfaces, subsequently to be anchored more positively by crosslinking the adsorbed enzyme layer in place.

Figure 4:
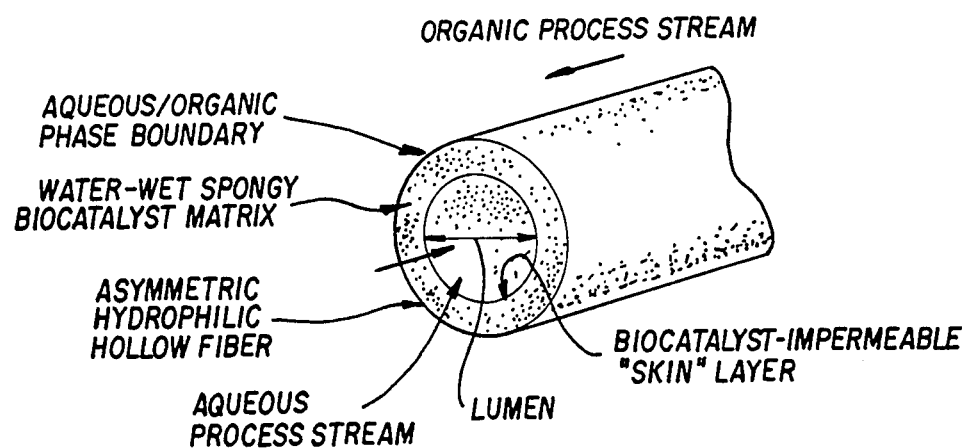
FIG. 4 is a schematic representation of a preferred embodiment of the invention wherein the enzyme is reversibly contained within an asymmetric, hydrophilic, and microporous hollow-fiber membrane.

In a preferred embodiment, the enzyme will be reversibly contained in a skinned, microporous membrane as described in the co-pending U.S. patent application Ser. No. 912,595 filed Oct. 1, 1986 and which is incorporated herein by reference. Such a membrane structure, shown in FIG. 4, is capable of entrapping the enzyme between two boundaries that it cannot cross under normal membrane reactor operating conditions. These two barriers consist of (1) the "skin" or surface layer of the enzyme-activated membrane, which contains pores that are sufficiently small so as to prevent the transport and leakage of macromolecular enzyme from the porous interior of the membrane to the aqueous process stream in contact with it and (2) the aqueous/organic phase boundary at the opposite membrane surface which, by virtue of the insolubility of most enzymes in organic solvents, prevents the enzyme from partitioning into and thus escaping from the membrane via the organic process stream. Such a membrane may be activated with enzyme by ultrafiltering an aqueous solution of enzyme through it, with very high loadings of active enzyme incorporated into porous membranes in this manner. An additional benefit of this mode of enzyme activation is its reversibility. That is, deactivated enzyme may simply be removed from the membrane by a back-flushing operation, thus facilitating the periodic replenishment of the enzyme catalyst.

An alternative preferred approach to enzyme activation of membranes for use in multiphase and extractive membrane reactor processes relies on the formation of dynamic enzyme-gel-polarized membranes atop the surface of ultrafiltration or gel-type membranes of the type used, for example, in hemodialysis and hemofiltration. Dialysis/ultrafiltration membranes comprised of regenerated cellulose or hydrophilic polyacrylonitrile-based polymers and copolymers are particularly preferred. Although such membranes are finely porous and hence water-permeable, the effective surface pore size of membranes suitable for use here are too small to admit enzymes. However, it has been demonstrated [Kerkhof, P. I. A. M., et al., "Enzymatic Hydrolysis of Lipids in a Membrane Reactor," a poster presented at the International Membrane Technology Symposium, Lund, Sweden, May 28-30, 1985; Molinari, R. and E. Drioli, Proc. Nat. Congr. Ind. Chem. Div. Sci., Siena, June, 10-25 1985] that such membranes can be effectively coated with enzymes by the simple expedient of ultrafiltering an aqueous enzyme solution across the membrane, thus leaving a concentrated enzyme gel layer deposited on one surface of the membrane film or fiber. If the organic process stream is subsequently brought into contact with the surface of the membrane so activated, the enzyme gel layer will tend to remain in place at the membrane surface, inasmuch as the enzyme is not appreciably soluble in organic solvents. In a refinement of this technique, we have further stabilized the enzyme surface layer or "dynamically formed membrane" by chemically crosslinking the enzyme protein.

4.3 Reaction and Resolution Process Parameters

In operation of the multiphase and extractive membrane reactor processes of this invention, two process streams, one aqueous (or first fluid) and the other consisting of a water-immiscible organic liquid or solution (or second fluid), are brought into contact with opposite faces of an enzyme activated membrane. Usually it is preferred that the enzyme-activated membrane be hydrophilic and thus wet by the aqueous phase in contact with it, since enzymes are typically more effective in aqueous environments than they are in organic solvents. Where the membrane is, in fact, water-wet, the fluid streams on either side of the membrane are preferably maintained at slightly different pressures such that a small positive pressure difference exists across the membrane, with the organic phase held at the greater pressure (e.g., by means of a back-pressure regulator or some other pressure control device).

When operated in this manner, the aqueous/organic phase boundary will be located at the surface of the membrane in contact with the organic process stream, and this location will be a stable one. Ultrafiltration of aqueous solution across the membrane will be prevented by the opposing pressure difference (i.e., organic-to-aqueous), but the hydrophilicity of the enzyme-activated membrane will ensure that the membrane is preferentially wet by the aqueous phase. The principal restriction on the magnitude of the organic-to-aqueous pressure difference (other than the requirement of mechanical membrane strength) is that it not exceed the intrusion pressure for penetration of membrane pores by the non-wetting organic phase, said intrusion pressure P being estimable from the Young-LaPlace equation as follows:

$$P = (2 \times \gamma / R_{pore}) \times \cosine \theta$$

where $\gamma$ the interfacial tension between the organic and aqueous phase, $R_{pore}$ is the effective pore radius, and $\theta$ is the three-phase contact angle between the membrane material and the fluids in contact with it. Typically, membrane pore sizes will be chosen such that the intrusion pressure will be at least several psi, preferably at least 10 psi, in order to provide a comfortable operating pressure window and to ensure stable operation of the enzyme-activated membrane in its role as a phase separator.

The feed stream that carries the initial reactants into the membrane module and into contact with the enzyme-activated membrane may either be organic and water-immiscible in nature (in which case the process is typically referred to as a "multiphase" membrane reactor process), or it may be aqueous (in which case the process is typically referred to as an "extractive" one). The flowrate of the feed stream is preferably adjusted so as to obtain the desired degree of enzymatic conversion of a key reactant (e.g., one of the stereoisomers in a racemic feed mixture, or the achiral precursor of a desired isomeric product). The flowrate of the stream on the opposite side of the membrane is preferably adjusted to permit one of the enzymatic reaction products to be withdrawn at an appropriate concentration.

For example, in a multiphase membrane reactor process where a reactant is sparingly water-soluble but the product species is highly so, it will be valuable to maintain the product stream flowrate at a relatively low value in order to concentrate the aqueous-phase product as much as possible; operation in this manner can accomplish product enrichment, i.e., removal of the aqueous-phase product at a concentration level higher than that of its organic-phase precursor. This minimizes the difficulty of any subsequent product concentration and/or purification steps that might be necessary. Conversely, in an extractive membrane reactor system where a key reactant is water-soluble and it is desirable to remove an inhibitory or unstable organic-soluble reaction product by extracting it into an organic solvent, it may be desirable to flow the organic process stream past the enzyme-activated membrane at a relatively high rate. Operation in this manner facilitates prompt and efficient removal of product from the enzymatic reaction zone, since high organic stream flowrates translate to low product concentrations. In this way, the yield and productivity of the enzymatic reaction are improved.

The relationship between the flowrates of the organic and aqueous process streams also exerts an important effect on the stereochemical purity of the products removed from the process. For example, in the case of multiphase membrane reactor process fed a racemic mixture of water-insoluble, organic-soluble stereoisomers, adjusting the organic feed steam flowrate so as to provide for very high conversion of one of the stereoisomers in the racemate will enhance the optical purity of the opposite isomer (i.e., the unreactive one) in the exiting organic process stream. By the same token, adjusting the flowrate of the aqueous product stream to effect significant enrichment of the water-soluble product will enhance the optical purity of this aqueous stream, since any of the opposite, relatively non-reactive isomer that dissolves in the aqueous phase will not be concentrated in this manner. Example No. 14 below illustrates these effects quite dramatically.

As shown in FIG. 7, recycle of at least one of the two streams exiting the enzyme membrane reactor may be indicated in order to permit racemization of the undesired or "off" isomer. For instance, in a continuous process (e.g., production of an optically pure acid or alcohol from a racemic ester), the molar feed rate of racemic reactant fed to the process and the molar rate of removal of the optically purified product will generally be equal under steady-state operating conditions, and the flowrate of the internal recycle stream will be inversely proportional to the per-pass conversion of the desired stereoisomer. In particular, the recycle stream flowrate will be set such that the per-pass conversion of the reactive stereoisomer times the molar rate of supply to the reactor of the desired stereoisomer in the combined make-up and recycle streams will equal the molar rate of removal of converted, purified stereoisomer in the product stream. In a batch process, the racemic reactant feed mixture will be charged to the system but once and will be recycled through the enzyme membrane reactor and racemization equipment (if required) until the reactive material (both the initial reactive stereoisomer and that derived from subsequent racemization of unreactive isomers) is depleted. When the enzyme stereoselectivity is less than absolute, there will frequently be a trade-off between the stereochemical purity of the product and the extent of recycle of the feed material. For example, the highest-optical-purity product will be obtained at low reactor conversions if the enzyme exhibits activity (albeit at different levels) toward both stereoisomers in the racemic feed, but operation at low per-pass conversion will typically involve high internal recycle rates and a significant investment in racemization and/or derivatization chemicals and process equipment.

Specific procedures have been established and published for the racemization (i.e., random inversion of the stereochemistry about a chiral carbon) and epimerization (i.e., the specific inversion of a chiral center to create an R-center from an S-center or vice versa) of many chiral compounds, and these can generally be employed without major modification in multiphase and extractive enzyme membrane reactor processes. For example, many chiral compounds may be racemized by heat (e.g., by subjecting them to refluxing conditions), either in aqueous solution, as neat organic liquids, or dissolved in organic solvents. Rates of racemization can frequently be accelerated through the us of either inorganic and organic acids (e.g., mineral acids, acetic anhydride, etc.) or bases (e.g., KOH or triethylamine). Where the term "racemization" is used herein, it is intended that it encompass both random racemization and specific epimerization processes.

The flows of the aqueous and organic process streams may be either cocurrent or countercurrent, and the membrane reactor process may be operated either batchwise (also, if desired, with recycle of one or both process streams), in a continuous mode, or in a semi-batch fashion. The details of the flow configuration can affect a number of secondary aspects of membrane reactor process performance including product purity, reactant conversion, phase separation, and pH control. It is not desired to direct the flow of the organic or aqueous process streams through the enzyme-activated membrane; rather, the convective flow of these immiscible process streams is preferably directed past the external surfaces of the membrane. Reactants are made to enter and products to leave the enzyme-activated membrane by diffusive processes in response to their local concentration gradients and consistent with their aqueous/organic partitioning behavor.

The temperature of the membrane reactor and of the aqueous and organic process streams fed to it will be maintained in a range optimal for enzyme activity and stability, as will be the solution pH. Where subsequent processing operations on one or both of the product streams exiting the membrane reactor dictate it (e.g., to effect on-line racemization or other chemical reaction of the "off" or undesirable isomer in a racemic mixture of stereoisomers to permit its recycle to the process), the temperature, pH, and other properties of the process stream may be adjusted outside of the range required for efficient enzyme operation. In this event, such streams must be returned to their original conditions of pH and temperature prior to being fed back into the membrane reactor itself. This is illustrated by the extractive membrane reactor process of FIG. 13, where the organic process stream containing the R-naproxen ester is contacted with an aqueous base that facilitates racemization and chemical hydrolysis of the ester, with the resulting aqueous stream containing the racemic naproxen acid isomers subsequently being acidified and recycled.

Under ideal circumstances, the "off" isomer in a racemic mixture will spontaneously racemize at enzymatic reaction conditions, in which case the provision of additional process steps and equipment for racemization and recycle operations can be avoided. Such is the case for the processes shown in FIGS. 14 and 15 for the production of optically purified amino acids and amino amides; here, the hydantoin and amino nitrile precursors racemize spontaneously.

Additional processing steps (e.g., repeated application of the membrane reactor process, recycling of the racemic mixture fluid and purification of unconverted reactants and/or products) may improve the efficiency of the multiphase/extractive membrane reactor process, and the chemical and stereochemical purity of the chiral products produced therein. For instance, where the optically resolved product exits a multiphase enzyme membrane reactor as an aqueous solution of the salt of a carboxylic acid (e.g., naproxen), this aqueous process stream may be pumped to a holding tank and acidified with a mineral acid in order to precipitate the acid in purified form from solution. Alternatively, the acidified product may be extracted into an organic solvent in a conventional solvent extraction operation, with the acid subsequently being isolated and purified by evaporation of the volatile organic solvent and attendant crystallization of the resolved acid product. When an optically purified organic-soluble product exits the membrane reactor in the organic process stream in the form of a neat organic liquid (e.g., R-glycidyl butyrate as shown in FIG. 16) or as a solution in a volatile organic solvent, the product may be further purified by distillation or by solvent evaporation. FIG. 16 further illustrates the recovery of minor amounts of an R-glycidyl butyrate impurity in the aqueous process stream exiting a multiphase membrane rector, wherein the aqueous stream is subjected to solvent extraction for separation and recovery of the preferentially organic-soluble butyrate ester from the larger quantities of water-soluble glycidol isomers present.

On occasion, the optically purified material produced in an enzyme membrane reactor will be an intermediate compound rather than the desired final product, and subsequent chemical reaction and product purification steps will be necessary. This is illustrated in FIGS. 14 and 15 where the D-carbamoyl amino acid and the D-amino amide intermediate products, respectively, are subjected to acid hydrolysis in order to recover the desired D-amino acid product in a chemically and stereochemically purified form.

Figure 2:
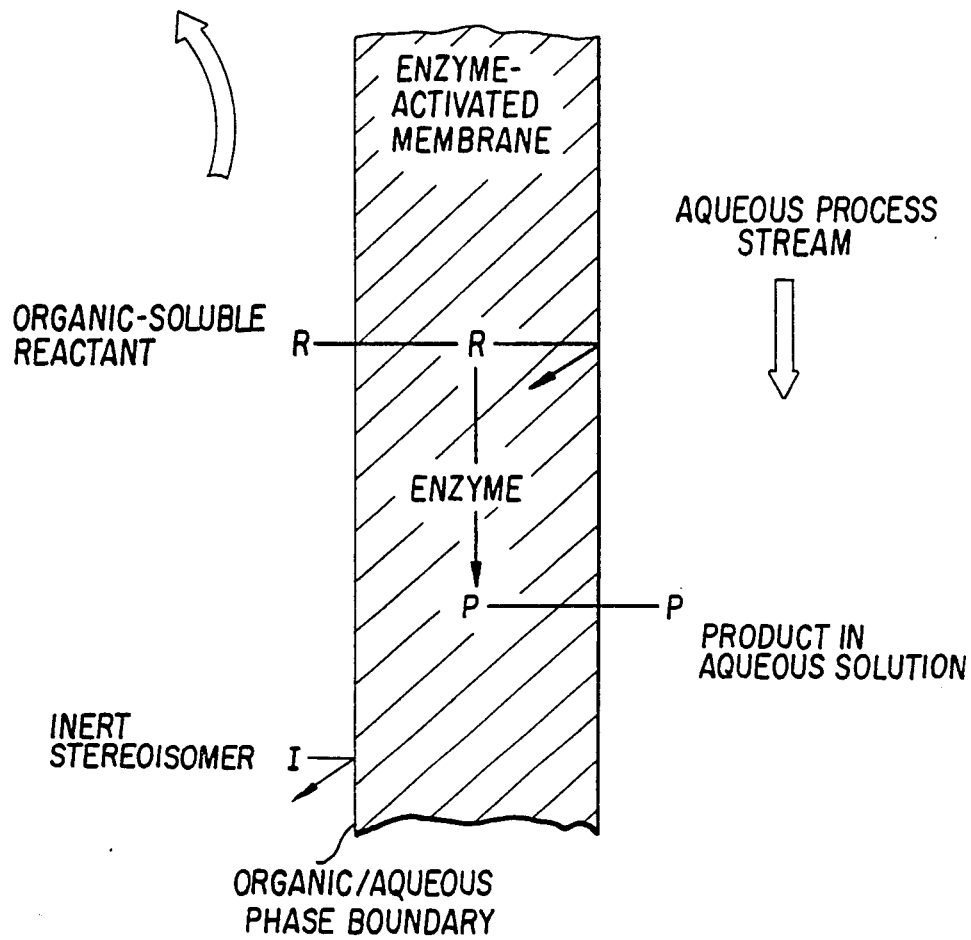
FIG. 2 is a schematic, cross-sectional view of the enzyme-activated membrane in a multiphase membrane reactor process, along with the organic and aqueous process streams in contact with it, for the purpose of illustrating the diffusion and reaction fluxes, as well as the phase partitioning behavior, of the various organic- and water-soluble participants in the reaction process.
Figure 3:
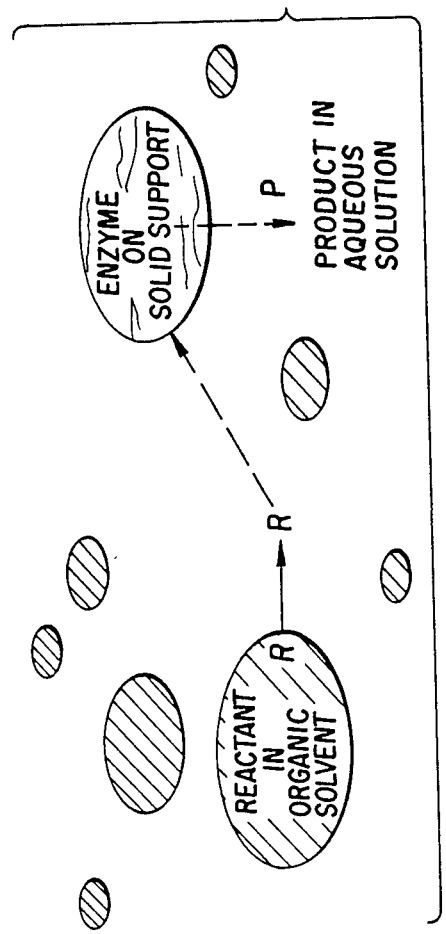
FIG. 3 shows, for purposes of comparison, the disposition of the three phases in conventional, dispersed-phase multiphase bioreactor operation.

In the application of this invention to the resolution of racemic mixtures of water-insoluble reactants as shown in FIGS. 2 and 5, the enzyme contained or otherwise immobilized upon or within the membrane is chosen to exhibit maximal stereoselectivity in the bioconversion of one or more but not all of the particular optical isomers present in the feed mixture. The reaction of poorly water-soluble isomers to at least one significantly more water-soluble reaction product is catalyzed by the enzyme within the membrane, and this water-soluble product is subsequently withdrawn in the aqueous process stream in a state of relatively high optical purity. At the same time, the mixture of feed isomers is depleted in that particular optical isomer which serves as the better substrate for the stereoselective enzyme, and in this manner the exiting organic-phase feed stream may simultaneously be optically purified and enriched in the non-reactive isomer with stereoconfiguration opposite from that of the aqueous-phase product species.

The net result is that an organic-phase mixture of R and S optical isomers is separated into two process streams, one of which i.e., the organic-phase product stream) contains the unconverted lipophilic isomer present in the original feed stream, while the aqueous stream contains the relatively water-soluble enzymatic reaction product possessing the opposite stereochemical configuration. In this manner, a feed stream containing a mixture of both R and S optical isomers is processed such that two "product" streams result, one of which is enriched in material with the R (or S) configuration while the other of which is enriched in material with the S (or R) configuration. Overall yields of the desired enantiomer of the product may be further enhanced by racemization of the material in one of the exiting streams, followed by its recycle to the inlet of the resolution process as shown in FIG. 7.

Figure 1:
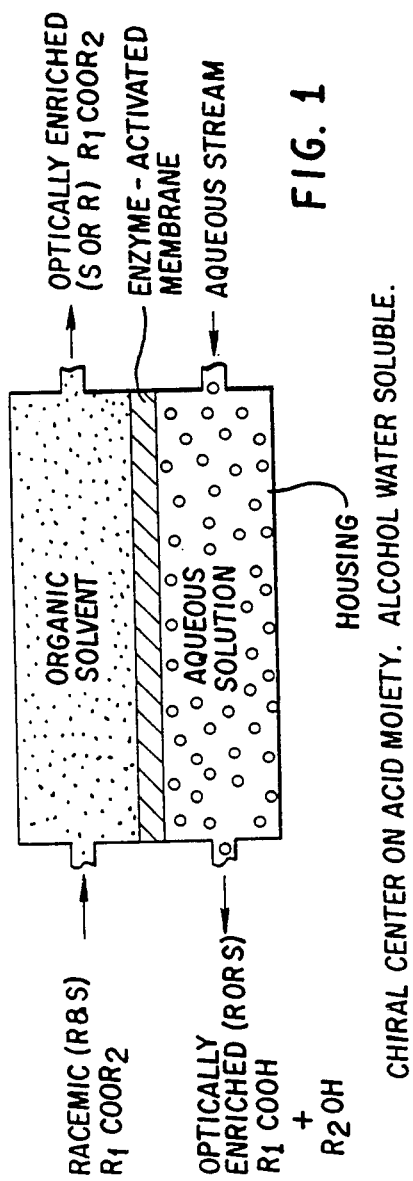

In the practice of the multiphase membrane reactor invention for stereochemical purification of a chiral ester or acid, a lipase or esterase enzyme would preferably be confined within a membrane, with the opposite faces being contacted by countercurrent streams of an aqueous solution (typically containing a low concentration of buffer) and an organic solvent containing a racemic mixture of sparingly water-soluble stereoisomers of a reactant ester as shown in FIGS. 1, 6, and 12. Because the organic acid is appreciably soluble in aqueous solution but not in organic solvent, and because the solubility characteristics of the organic ester are precisely the opposite, optically purified product acid can be carried out of the multiphase membrane reactor in the aqueous process stream, preferably at high concentration (i.e., implying a low aqueous stream flowrate), while the relatively non-reactive stereoisomer of the racemic ester feed mixture will preferentially remain in the organic stream. Product separation and enrichment are accomplished by operating the reactor with organic solvents that provide optimal partitioning selectivity between reactants and products and at high organic-/aqueous phase ratios that facilitate concentration of the product in the aqueous process stream.

On the one hand, where it is the less enzymatically reactive ester that has the "correct" i.e., biologically active) stereochemical configuration, it may be withdrawn from the process in the organic phase and isolated; if it is the acid form of this isomer which is desired, the optically purified ester may be chemically hydrolyzed to yield the optically purified acid as the desired product. Meanwhile, the carboxylic acid (and alcohol) product in the aqueous phase, depleted in material with the desired stereochemical configuration and thereby enriched in the undesired material, may optionally be re-esterified and subjected to racemizing conditions prior to recycle to the process. On the other hand, where it is the more enzymatically reactive ester that has the "correct" stereochemical configuration, the desired product will be found in the form of the optically purified acid, which may be isolated and chemically reconverted to the corresponding optically purified ester derivative, if desired, under non-racemizing re-esterification conditions.

Thus, the above-described multiphase membrane reactor process separates an organic-phase mixture of R and S esters into two process streams, with the organic stream containing the unconverted stereoisomer of the lipophilic ester present in the original feed stream, and the aqueous stream containing the relatively water-soluble acid isomer possessing the opposite stereochemical configuration. In this manner, a feed stream containing a mixture of both R and S esters is processed such that two "product" streams result, one of which is enriched in material with the R configuration while the other of which is enriched in material with the S configuration. If the enzyme is active towards the S form of the ester as shown in FIG. 6, and if the R-isomer is the desired product, then it will be recovered from the exiting organic process stream, either directly or in the form of the R-ester or indirectly as the R-acid, after chemical hydrolysis. If it is the S-isomer which is required, then material with this stereochemical configuration may be isolated from the aqueous process stream, either directly in the form of the S-acid or indirectly as the S-ester, following re-esterification of the resolved acid under non-racemizing conditions that preserve its stereochemistry.

FIG. 1 illustrates a particular multiphase enzyme membrane reactor process for the resolution of racemic esters and acids wherein the chiral center resides on the acid moiety. However, multiphase enzyme membrane reactors of this type may also be applied to the optical resolution of racemic esters and alcohols in cases wherein the chiral carbon resides on the alcohol moiety; in these situations, the alcohol may be either preferentially water-soluble or organic-soluble. In particular, FIG. 11 shows a generic example wherein the alcohol is chiral and preferentially organic-soluble, whereas FIG. 16 shows a specific case, namely the resolution of a racemic ester (R-glycidyl butyrate), wherein the alcohol component is chiral but preferentially water-soluble.

FIGS. 8 and 9 depict operation of an extractive enzyme membrane reactor process for the resolution of a racemic feed mixture of water-soluble acids and the attendant production of optically purified aqueous acid and organic ester streams. It is presumed in FIGS. 8 and 9 that the chiral center of interest resides on the acid moiety rather than on the alcohol, which is not shown. In operation, a stereoselective enzyme capable of catalyzing an esterification reaction (e.g., a lipase or esterase) is contained within or immobilized upon a phase-separating membrane, with its opposite faces being contacted by two countercurrent streams, the first being an aqueous feed solution containing a racemic mixture of water-soluble, organic-insoluble acids and the second stream being a water-immiscible organic solvent capable of extracting the ester reaction product into it. The flowrate of the organic extractant is maintained sufficiently high so as to keep the aqueous-phase concentration of the inhibitory ester product very low. In this way, the thermodynamically unfavorable, product-inhibited bioconversion of an acid to an ester in aqueous media can be carried out to high conversion with reasonable productivity.

In the particular process depicted in FIG. 8, depending on the enzyme stereoselectivity (i.e., whether the enzyme is most active in the synthesis of the R- or of the S-form of the ester), either the R (or S) ester is preferentially removed from the extractive enzyme membrane reactor in the organic phase. This organic product stream contains relatively little S (or R) material due to the R (or S) stereoselectivity of the enzyme and due to the poor organic-phase solubility of the acid stereoisomers. At the same time, the aqueous-phase product stream is depleted in the R (or S) acid that has been enzymatically converted to ester, and this aqueous stream is therefore correspondingly optically enriched in the S (or R) acid stereoisomer. As explained in more detail in conjunction with the description of the multiphase membrane reactor embodiment of this invention, it is similarly possible to operate an extractive membrane reactor in an esterification mode using an enzyme with either R- or S-selectivity so as to produce either the S- or the R-form of a chiral acid, alcohol, or ester. This is accomplished by combining the extractive membrane reactor process with appropriate chemical derivatization, hydrolysis, racemization, and/or product isolation steps as detailed above. Analogous extractive membrane reactor processes can similarly be applied to the resolution or asymmetric synthesis of chiral compounds other than acids, alcohols, and esters.

Finally, multiphase and extractive membrane reactor processes of the types shown in FIGS. 2 and 9, but without the presence of unreactive stereoisomers in the feed, may also be used to effect the selective conversion of achiral organic compounds to purified stereoisomers, particularly where the achiral precursor and the chiral product of the enzymatic reaction are soluble in different phases.

When the achiral precursor is sparingly water-soluble, it may be fed to a multiphase enzyme membrane reactor either as the neat liquid or in a water-immiscible organic solution, to be stereoselectively converted upon contact with the enzyme-activated membrane to a preferentially water-soluble product (see FIG. 2). A particular application of this type of multiphase membrane reactor process would be to the stereoselective hydrolysis of water-insoluble, symmetric diesters to chiral, water-soluble acid ester products, as catalyzed by pig liver esterase. In this application, the achiral diester reactant would be fed to the multiphase membrane reactor in the organic phase, and the chiral and optically purified acid ester product would be withdrawn in the aqueous phase on the opposite side of the phase-separating membrane.

When the achiral precursor is preferentialy water-soluble and the chiral product organic-soluble, the achiral reactant may be fed to an extractive enzyme membrane reactor as an aqueous solution in contact with one surface of an enzyme-activated membrane. The resulting organic-soluble chiral reaction product is subsequently extracted into a stream of organic solvent in contact with the opposite surface of the membrane, and it is removed from the reactor in this organic stream. An example of the application of this type of extractive membrane reactor system is the asymmetric synthesis of organic-soluble D-mandelonitrile from achiral precursors—namely, neat benzaldehyde and an aqueous methanolic solution of hydrogen cyanide—using D-oxynitrilase (E.C. 4.1.2.10) as the biocatalyst. This enzyme catalyzes the asymmetric, stereoselective addition of HCN across the carbonyl double bond of benzaldehyde.

Other multiphase and extractive enzyme membrane reactors based on stereoselective ammonialyase and transaminase enzyme chemistries are useful in the synthesis of optically purified amino acids from achiral precursors such as trans-cinnamic acid and ammonia (i.e., achiral precursors of L-phenylalanine) and alpha-keto acids, particularly if complexing agents are emplyed to increase the organic-phase solubilities of the amino acid products. In the ammonia lyase-catalyzed production of phenylalanine, ammonia is asymmetrically and stereoselectively added across the carbon-to-carbon double bond of trans-cinnamic acid.

The present invention, therefore, provides efficient means for the enzymatic resolution or enzymatic synthesis of chiral amides, acids, alcohols, amines, nitriles, hydantoins, and other valuable chiral compounds in multiphase and extractive membrane-mediated enzymatic reaction systems. The above description of the operation of these enzyme membrane reactors, and description of the examples which follow, are meant only to suggest the breadth of potential applications of the invention in the production of stereochemically pure compounds, and they are by no means limiting as to the scope of the invention or the modes of operation intended for these multiphase and extractive membrane reactor processes.

4.4 Examples

Examples of the practice of the invention and elements thereof are as follows. As used herein the letter "u" alone or as a prefix is intended to mean "micro."

4.4.1 Example No. 1—Naproxen Resolution

A multiphase bioreactor was prepared using a 0.85m$^2$ custom made solvent-resistant membrane module fabricated with polyacrylonitrile, ultrafiltration hollow fibers from Asahi Medical Company PAN-200 hemofilter. The enzyme, a lipase derived from *Candida cylindracea*, was purchased from Genzyme Corporation, with a specific activity of 10,500 units/mg (1 unit=1 umol of fatty acid liberated from olive oil per hour at 37° C. and pH 7.7). This enzyme is known to hydrolyze stereoselectively esters of Naproxen (2-(6-methoxy-2-naphthyl) propionic acid).

3.0 grams of the lipase were dissolved in 500 mls of distilled water; this solution was recirculated in an ultrafiltration mode from the shell into the lumen and back to the reservoir for 30 minutes. The ultrafiltrate was then collected until the resevoir was empty, and methyl isobutyl ketone (MIBK) was then pumped into the shell and recirculated at 400–450 ml/min with a 5–7 psig shell pressure to remove any remaining enzyme solution from the shell. A sample of the ultrafiltrate was assayed on triacetin, showing that less than 5% of the enzymatic activity remained, compared to the starting solution. Two hundred milliliters of potassium phosphate buffer (25 mM, pH 8.5) were recirculated through the shell at 350–400 ml/min.

The methyl ester of racemic Naproxen was synthesized. It should be noted that the water solubility of this ester is roughly 0.1–0.2 mM while its solubility in MIBK is about 1.3 M. 42 grams of the solid Naproxen ester were slowly added to the MIBK to achieve a final concentration of 0.75M with a total organic volume of roughly 225 ml. The pH was controlled at 8.50±0.01 with 0.25 M NaOH using a Brinkman Dosimat 665 pH-stat.

The reaction was monitored by periodically withdrawing aqueous samples and determining the Naproxen concentration spectophotometrically ($E_{320}=1250$). The average rate for the first 45 minutes was 35 umol/hr. The hydrolytic rate for the next 36 hours was in the range of 9 to 14 umol/hr.

4.4.2 Example No. 2—Ibuprofen Resolution

A reactor was prepared as described in Example 1 (Naproxen) using essentially the same mode of loading the enzyme, 3.0 grams of Candida lipase (Genzyme Corporation) were ultrafiltered from the shell into the lumen. The enzyme was then washed with 2-3 liters of distilled water and 1 liter of potassium phosphate buffer (0.10 M, pH 7.7). The module was then drained.

The trifluorethyl ester of racemic Ibuprofen (2-(4-isobutylphenyl)-propionic acid) was synthesized. The water solubility of the ester is roughly 0.4 mM. Two hundred and sixty-five grams of the liquid Ibuprofen ester were pumped into the shell of the reactor and recirculated at 400-450 ml/min with an outlet pressure of 5-8 psig. No organic solvent was required as the substrate is already a water-immiscible liquid. Phosphate buffer was immediately pumped into the lumen and recirculated at 400-450 ml/min. The aqueous volume was about 650 mls, and the pH was controlled at 7.7±0.01 with 1.0M NaOH.

The reaction was monitored by following acid production based on hydroxide titration data. The average hydrolytic rate for the first 60 minutes was 160 umol/min. The aqueous buffer was replaced after 76 minutes and acidified to pH 2.0 with concentrated HCl in the presence of about 200 ml of chloroform. The chloroform was washed with a saturated sodium chloride solution and dried with magnesium sulfate. The Ibuprofen solution was evaporated to dryness, and 2.13 gms of crude Ibuprofen were recovered. Over the next 76 hours, the average hydrolysis rate was 21 umol/min as measured by titrimetry. This corresponded to about 9.8% conversion to acid. The aqueous reservoir was changed six times over this period, yielding about 15 grams of Ibuprofen. This material was recrystallized from hexane. The material has a melting point of 51°-53° C. (literature value for (s)-Ibuprofen 50°-52° C. while racemic Ibuprofen 75°-77° C.). The specific optical rotation of this material was $[\alpha]_D = +55.0°$ (c=1, $C_2H_5OH$).

4.4.3 Example No. 3—Olive Oil Hydrolysis

A reactor was prepared using a polyacrylonitrile hemofilter made by Asahi Medical Company (Model PAN 150) containing 1.0 $m^2$ membrane area. The enzyme used was *Candida cylindracea* lipase (Sigma Chemical Co., specific activity 700 units/mg). This enzyme is reported to have no positional specificity; hence, it will hydrolyze triglycerides such as olive oil, to free fatty acids and glycerol. An enzyme solution was prepared by dissolving 5.0 grams of Candida lipase in 1 liter of distilled water. This solution was recirculated in an ultrafiltration mode from the shell into the lumen and back to the reservoir for 90 minutes. The ultrafiltrate was then filled with hexane to push out all the remaining water from the shell.

The hexane was rinsed from the shell with several volumes of edible olive oil (Welch, Holmes & Clark Co.) and the lumen was rinsed with 400 ml of distilled water. The olive oil was recirculated through the shell at 250 ml/min with 8-12 psig inlet pressure and the total oil volume was about 250 mls. The water phase was recirculated at 80 ml/min with a total volume of 270 ml. The module and both reservoirs were immersed in a 37° C. water bath.

Oil samples were periodically withdrawn and analyzed for free fatty acids by titration with 50 mM ethanolic sodium hydroxide. After 24 hours of emulsion-free operation, the oil phase was determined to contain 3.45 mmol of acid per gram, corresponding to about 97% conversion of the triglyceride. The pH of the aqueous phase steadily dropped during the run from 6.4 to 5.7 and the final glycerol concentration was about 8% as measured by refractometry.

4.4.4 Example No. 4—Olive Oil Hydrolysis

A reactor was prepared as described in the above example using essentially the same loading procedure except 3.8 grams of Candida lipase were used. This enzyme was then crosslinked in the membrane by recirculating a 2.5% glutaraldehyde solution through the shell for 3 hours. After 3 hours, the shell and lumen were rinsed out with several volumes of distilled water. The shell was filled with 275 ml of olive oil and recirculated at 340 ml/min with a 8 psig inlet pressure. The water phase had a volume of 275 ml and was recirculated at 80 ml/min.

After 22 hours of emulsion-free operation at room temperature, the organic sample contained 1.16 mmol of free fatty acid per gram, corresponding to a 33% conversion of the olive oil.

4.4.5 Example No. 5—Olive Oil Hydrolysis

A reactor was prepared using a regenerated cellulose, hollow fiber kidney manufactured by Asahi Medical Co. (Model AM100L) containing 0.8 $m^2$ of membrane area. A Candida lipase solution was prepared by dissolving 3.0 grams of enzyme in 500 ml of 0.1 M sodium chloride. The enzyme solution was recirculated through the lumen back into the reservoir at 70 ml/min and the permeate was collected from the shell until the reservoir was empty. The enzyme was rejected by the membrane (molecular weight cutoff roughly 1,000) and accumulated on the membrane as a gel layer. This enzyme was then crosslinked using 2.5% glutaraldehyde as described in the above example.

After 3 hours, the glutaraldehyde was rinsed out with several volumes of distilled water. The lumen was then rinsed with several volumes of olive oil to remove the residual water. The olive oil was recirculated in the lumen at 40 ml/min with an inlet pressure of 8 psig and the total volume was about 200 ml. The water phase was recirculated at 20 ml/min with a total volume of 200 m.

After 4 hours of emulsion-free operation, the oil was determined to contain 0.35 mmol of acid per gram, corresponding to a 10% conversion of the olive oil.

4.4.5 Example No. 6—Phenoxyacetate Methyl Ester Hydrolysis

An enzyme solution was prepared by dissolving 50 grams of *Candida lipase* (Mol. Wt. 100,000; Sigma Chemical Co. Cat #L 1754) in 1.25 liters of water and then filtering this solution to remove the insoluble material. This interfacially acting enzyme is known to hydrolyze a large number of organic esters, among them, phenoxyacetate methyl ester and amyl acetate.

The enzyme was loaded into a 0.85 $m^2$ custom-made solvent-resistant membrane module fabricated with anisotropic polyacrylonitrile (PAN) hollow fibers taken from a PAN-200 hemofilter (ASAHI Medical Co.). The morphology of this membrane is such that it can be described as an asymmetric hydrophilic inside-skinned hollow fiber characterized by 90% rejection of proteins with a molecular weight higher than 50,000. The enzyme solution was recirculated from the shell side to the lumen side and back to the solution reservoir in an ultrafiltration mode. Throughout the loading process the pressure difference between the shell and lumen compartments was kept to 8 psi by adjusting the ultrafiltration rate (generally between 200 to 20 ml/min). The procedure was completed in one hour. The initial and final enzyme solution activities are shown below:

|  | Specific activity*<br>u mole/min-ml | Total activity<br>u mole/min |
|---|---|---|
| Initial solution | 7.84 | 9800 |
| Final solution | 0.05 | 63 |

*determined by measuring the rate of addition of 25 mM NaOH required to maintain the pH at 7.8 in a solution of 20 ml of 0.2 M NaCl + 0.5 ml of phenoxyacetate methyl ester (Aldrich Co.) + 2.5 ml of enzyme solution.

After loading the enzyme into the reactor, recirculation of 1140 ml of phenoxyacetate methyl ester on the shell side was started. The solubility of this ester in water is approximately 25 mM. The recirculation rate was 150 ml/min and the average pressure on the shell compartment was kept at 6.5 psi by adjusting a throttling valve at the shell side exit. On the lumen side 2 liters of 0.1 M NaHCO$_3$ were recirculated at a rate of 300 ml/min. The pH of the aqueous reservoir was kept at 7.8 by addition of 50% NaOH. The reactor was run continuously for five days with daily replacement of the buffer and reaction products solution in the aqueous-phase reservoir. Throughout the experiment, enzyme assays of the buffer reservoir showed no detectable enzymatic activity in the aqueous phase.

The reaction progress and rate were monitored by following the caustic consumption and observing the organic phase reservoir level. At the beginning of the experiment the rate of ester hydrolysis was 3000 umoles/min and at the end it was 1500 umoles/min. The phenoxyacetic acid product in the aqueous reservoirs was subsequently recovered by acidifying to a pH of 1.0 with concentrated HCl and filtering the precipitated solids. After drying, the solids were assayed titrimetrically and found to be 96.3 % acid. A sample of the dried solids was dissolved in a mixture of chloroform and water with a subsequent drying/evaporation of the chloroform phase. The remaining solid from this purification step was titrimetrically assayed to be 99.5% pure with a melting point of 98°-103° C. (melting point of phenoxyacetic acid is 98°-100° C.). The total amount of phenoxyacetic acid recovered was 0.953 kilogram.

4.4.7 Example No. 7—Amyl Acetate Hydrolysis

Using the same membrane module described in Example 6 with the enzyme still in the membrane, the hydrolysis of amyl acetate was conducted. The solubility of this ester in water is approximately 13 mM. Recirculation of 400 ml of amyl acetate on the shell side was started and as before, the recirculation rate was 150 ml/min and the average pressure on the shell compartment was kept at 6.5 psi by adjusting a throttling valve at the shell side exit. On the lumen side 1 liter of 0.05 M NaHCO$_3$ was recirculated at a rate of 300 ml/min. The pH of the aqueous reservoir was kept at 7.8 by addition of 5.57 M NaOH. The rate of amyl acetate hydrolysis was determined to be 250 umoles per minute. Once the rate of amyl acetate hydrolysis was measured the reaction was stopped and the system rinsed with water both on the lumen and the shell side. The reactor was then backflushed for 15 hours with filtered (0.2 μm filter) tap water entering on the lumen side and exiting on the shell side at a flow rate of 50 ml/min. Two liters of 8 M urea were backflushed in the same manner as the tap water and then both the shell and lumen compartments were rinsed with 4 liters of distilled water.

The rate of amyl acetate hydrolysis in the reactor was measured in exactly the same manner described above with the exception that 25 mM NaOH was used. The reaction rate was 6.8 umoles per minute which corresponds to 3% of the initial activity.

4.4.8 Example No. 8—Amyl Acetate Hydrolysis

At the conclusion of the membrane regeneration procedure described in Example 7, the module was charged with 20 grams of Candida lipase (the same type and in the same concentration described in Example 6). Amyl acetate was used as a substrate and the reactor operated in exactly the same manner as described in Example 7. The rate of reaction was measured at 70 umoles/min.

4.4.9 Example No. 9—Ethyl Butyrate Hydrolysis

An enzyme solution was prepared by dissolving 10.8 ml of a pig liver esterase preparation (Mol. Wt. 150,000, 11 mg/ml, Sigma Chemical Co., Cat #E 3128) in 300 ml of 0.2 M phosphate buffer pH 8.0. This enzyme, falling under the category of an esterase, will hydrolyze ethyl butyrate dissolved in water, i.e., the reaction is a homogeneous one and does not require an organic/aqueous interface to be present.

The enzyme was loaded into the same membrane module described in Example 6 by recirculating the enzyme solution from the shell side to the lumen side and back to the solution reservoir in an ultrafiltration mode. Throughout the loading process the pressure difference between the shell and lumen compartments was kept to 9.5 psi by adjusting the ultrafiltration rate (generally between 200 to 20 ml/min). The procedure was completed in one hour. The initial and final enzyme solution activities are shown below:

|  | Specific activity*<br>u mole/min-ml | Total activity<br>u mole/min |
|---|---|---|
| Initial solution | 49.2 | 14800 |
| Final solution | 0.51 | 153 |

*determined by measuring the rate of addition of 20 mM NaOH required to maintain the pH at 8.0 in a solution of 20 ml of 0.1 M phosphate buffer pH 8.0 + 0.2 grams of ethyl butyrate (Aldrich Co.) + 1.0 ml of enzyme solution.

After loading the enzyme to the reactor, recirculation of 500 ml of ethyl butyrate on the shell side was started. The solubility of this ester in water is 59 mM. The recirculation rate was 500 ml/min and the average pressure on the shell compartment was kept at 6.5 psi by adjusting a throttling valve at the shell side exit. On the lumen side, 1 liter of 0.2 M phosphate buffer pH 8.0 was recirculated at a rate of 500 ml/min. The pH of the aqueous reservoir was kept at 8.0 by addition of 6.0 M NaOH. The rate of ethyl butyrate hydrolysis was determined to be 9600 umoles per minute. Once the rate of ethyl butyrate hydrolysis was measured, the reaction was stopped and the system rinsed with water both on the lumen and the shell side.

The enzyme was removed from the reactor through the following procedure:
  backflushed with 6 liters of distilled water entering on the lumen side and exiting on the shell side at a flow rate of 50 ml/mn
  rinse on both the shell and lumen side with
    (a) 4 liters of 1.0 M NaCl
    (b) 500 ml of 12% $(NH_4)_2SO_4$
    (c) 500 ml of 8 M urea
    (d) 2 liters of 1.0 M NaCl.

The rate of ethyl butyrate hydrolysis in the reactor was measured in exactly the same manner described above with the exception that 25 mM NaOH was used. The reaction rate was 30 umoles per minute corresponding to 0.3% of the initial activity in the module.

4.4.10 Example No. 10—BTEE Hydrolysis

An enzyme solution of Chymotrypsin (Mol. Wt. 23,000, Sigma Chemical Co. Cat #C 4129) was prepared by dissolving 0.5 grams of the enzyme in 1 liter of 0.1 M $K_2HPO_4$/1.0 M NaCl pH 7.8. This solution was recirculated on the shell side of a 1 $m^2$ ASAHI PAN-150 hemofilter (ASAHI Medical Co.) at a flow rate of 50 ml/min for 1 hour. Because there was no flow of enzyme solution from the shell to the lumen side, the enzyme was loaded into the membrane solely in a diffusive mode. After draining the shell side of the enzyme solution, recirculation of 1 liter of silicone oil (Petrarch Systems Inc.) was started on the shell compartment while maintaining a pressure of 9 psi. A 0.2 mM solution of N-Benzoyl-L-Tyrosine Ethyl Ester (BTEE, Sigma Chemical Co.) in 0.1 M $K_2HPO_4$/1 M NaCl pH 7.8 was then passed through the lumen side of the module at a flow rate of 1 l/min. The activity of the module was calculated by measuring the amount of BT acid that was present in the aqueous effluent from the reactor. The module activity was determined to be 80 umoles/min. The membrane module was then drained of solvent and buffer and backflushed with 10 l of 0.1 M phosphate buffer. The membrane module activity was measured in the same manner described above with the exception that the BTEE solution was pumped into the reactor at a rate of 53 ml/min. The activity of the membrane module was 4 umole/min corresponding to 5% of the initial activity.

4.4.11 Example No. 11—BTEE Hydrolysis

An enzyme solution was prepared by dissolving 100 mg of the same Chymotrypsin used in Example 10 in 500 ml of 0.1 M phosphate buffer pH 7.0. The enzyme was loaded on a 1 $m^2$ ASAHI PAN-150 hemofilter identical to the one used in Example 10 by recirculating the enzyme solution from the shell side to the lumen side and back to the solution reservoir in an ultrafiltration mode. The procedure was completed in 2.5 hours.

After loading the enzyme to the reactor, recirculation of 1 liter of 10 mM BTEE in amyl acetate was started on the shell side. The recirculation rate was 10 ml/min and the average pressure on the shell compartment was kept at 6.5 psi by adjusting a throttling valve at the shell side exit. On the lumen side, 200 ml of 2 mM phosphate buffer pH 7.8 was recirculated at a rate of 250 ml/min. The pH of the aqueous reservoir was maintained at 7.8 by addition of 1 M NaOH. The initial rate of BTEE hydrolysis was determined to be 45 umoles/min.

4.4.12 Example No. 12—BTEE Hydrolysis

In order to increase the amount of Chymotrypsin that is retained by the hollow fibers used in Examples No. 6-11, the molecular weight of the enzyme was increased by crosslinking with Bovine Serum Albumin (Sigma Chemical Co., Cat #A 4503) using glutaraldehyde and following conventional protocols for such chemistry. Gel permeation chromatography revealed that over 80% of the protein conjugate had a molecular weight in excess of 100,000. The final enzyme solution consisted of 1 liter of 0.1 M $K_2HPO_4$/1 M NaCl pH 7.8 with a BTEE activity of 10 umoles/min-ml. The enzyme was loaded on a 1 $m^2$ ASAHI PAN-150 hemofilter identical to the one used in Example 10 by ultrafiltering the solution once through from the shell side to the lumen side at a flow rate of 20 ml/min.

After loading the enzyme to the reactor, recirculation of 500 ml of 40 mM BTEE in n-octanol (Aldrich Co.) was started on the shell side. The recirculation rate was 500 ml/min and the average pressure on the shell compartment was kept at 6.5 psi by adjusting a throttling valve at the shell side exit. On the lumen side, 1 l of 0.1 M $K_2HPO_4$/1 M NaCl buffer pH 7.8 was recirculated at a rate of 500 ml/min. The pH of the aqueous reservoir was maintained at 7.8 by addition of 1 M NaOH. The initial rate of BTEE hydrolysis was determined to be 700 umoles/min.

Example No. 13—Resolution of 2-Chloropropionic Acid

Racemic 2-chloropropionate octyl ester was prepared by reacting 130 gm (1.0 mole) of n-octanol with 127 gm (1.0 mole) of 2-chloropropionyl chloride in 240 ml of pyridine and 50 ml of tetrahydrofuran. The reaction was carried out for 24 hours after which the solution was washed with 500 ml of: (1) 1N HCl, 2) saturated solution of $NaHCO_3$, and (3) saturated solution of NaCl. The organic phase was finally dried over $MgSO_4$. The total weight of 2-chloropropionate octyl ester obtained was 210 gm (0.96 mole).

An enzyme solution was prepared by dissolving 30 grams of Candida lipase (Mol. Wt. 100,000; Sigma Chemical Co. Cat #L 1754) in 0.75 ml of water and then filtering this solution to remove the insoluble material. The enzyme was loaded into a 0.85 $m^2$ custom-made solvent-resistant membrane module fabricated with anisotropic polyacrylonitrile (PAN) hollow fibers taken from a PAN-200 hemofilter (ASAHI Medical Co.). The morphology of this membrane is such that it can be described as an asymmetric hydrophilic inside-skinned hollow fiber characterized by 90% rejection of proteins with a molecular weight higher than 50,000. The enzyme solution was recirculated from the shell side to the lumen side and back to the solution reservoir in an ultrafiltration mode. Throughout the loading process the pressure difference between the shell and lumen compartments was kept to 8 psi by adjusting the ultrafiltration rate (generally between 200 to 20 ml/min). The procedure was completed in one hour.

After loading the enzyme to the reactor, recirculation of 210 gm. (0.96 mole) of racemic 2-chloropropionate octyl ester on the shell side was started. The solubility of this ester in water is approximately 1.2 mM. The recirculation rate was 400 ml/min and the average pressure on the shell compartment was kept at 6.5 psi by adjusting a throttling valve at the shell side exit. On the lumen side 1 liter of 0.05 M $K_2PO_4$ was recirculated at a rate of 400 ml/min. The pH of the aqueous reservoir was kept at 7.0 by addition of 1 M NaOH. The reactor was run continuously for 6.8 days.

The reaction progress and rate were monitored by following the caustic consumption. At the beginning of the experiment the rate of ester hydrolysis was 186 umoles/min and at the end it was 25 umoles/min. The experiment was terminated when 41% of the initial ester had been hydrolyzed. The optical rotation of the final ester mixture was $[\alpha]_D = -0.41°(c=50, CHCl_3)$. The initial ester substrate to the reactor had no optical rotation.

4.4.14 Example No. 14—Resolution of N-benzoyl-tyrosine Ethyl Ester

Racemic N-benzoyl-tyrosine ethyl ester was prepared by dissolving 25 gm of N-benzoyl-L-tyrosine ethyl ester (Sigma Chemical Co.) in 400 ml of dry ethanol and adding 400 ml of ethanol in which 5.6 gm of sodium had been previously dissolved. This solution was stirred overnight under argon. The solution was subsequently mixed with 1 L of water and the equivalent amount of HCl necessary to neutralize the NaOH generated by the sodium. This solution was then extracted with chloroform and the chloroform was subsequently washed with bicarbonate buffer and finally dried over $MgSO_4$. The chloroform was evaporated leaving 14.2 gm of a solid which had a melting point of 125°–126° C. and no optical rotation. This solid was racemic BTEE (mp for L-BTEE 118°–121° C.).

Four grams of Chymotrypsin (Sigma Chemical Co.) were immobilized in a 1 $m^2$ PAN-150 hemofilter (ASAHI Medical Co.) by adsorbing the enzyme on the hollow fibers and then crosslinking the enzyme with a 2.5 % glutaraldehyde solution in 0.05 M phosphate buffer pH 7.0.

After loading the enzyme to the reactor, recirculation of 1.13 liters of a 29.8 mM racemic BTEE in n-octanol solution on the shell side was started. The recirculation rate was 400 ml/min and the average pressure on the shell compartment was kept at 6.5 psi by adjusting a throttling valve at the shell side exit. On the lumen side 0.21 liter of 0.1 M $K_2PO_4$ were recirculated at a rate of 400 ml/min. The pH of the aqueous reservoir was kept at 7.8 by addition of NaOH. The reactor was run continuously for 18 hours.

At the conclusion of the experiment both the organic and aqueous phases were analyzed and the results are shown in Table I.

TABLE I

| SPECIES/PHASE | INITIAL | | FINAL | |
|---|---|---|---|---|
| | CONC (mM) | mMOLES | CONC (mM) | mMOLES |
| D-BTEE/Org | 14.9 | 16.8 | 14.9 | 16.79 |
| L-BTEE/Org | 14.9 | 16.8 | 0.0 | 0.0 |
| L-BT/Org | 0.0 | 0.0 | 0.12 | 0.14 |
| D-BTEE/Aq | 0.0 | 0.0 | 0.07 | 0.01 |
| L-BTEE/Aq | 0.0 | 0.0 | 0.0 | 0.0 |
| L-BT/Aq | 0.0 | 0.0 | 80.0 | 16.7 |

Organic phase enantiomeric excess = 98%
Aqueous phase Enantiomeric excess = 99.8%

4.4.15 Example No. 15—Resolution of N-Acetyl-Tyrosine Ethyl Ester

Four grams of Chymotrypsin (Sigma Chemical Co.) were immobilized in a 1 $m^2$ PAN-150 hemofilter (ASAHI Medical Co.) by adsorbing the enzyme on the hollow fibers and then crosslinking the enzyme with a 2.5 % glutaraldehyde solution in 0.05M phosphate buffer pH 7.0.

After loading the enzyme to the reactor, recirculation of 1 liter of a 2.86 mM racemic ATEE (Sigma Chemical Co.) in n-octanol solution on the shell side was started. The recirculation rate was 400 ml/min and the average pressure on the shell compartment was kept at 6.5 psi by adjusting a throttling valve at the shell side exit. On the lumen side 0.15 liter of 0.1M $K_2PO_4$ were recirculated at a rate of 400 ml/min. The pH of the aqueous reservoir was kept at 7.8 by addition of NaOH. The reactor was run continuously overnight.

From the known amount of base consumed (1.43 mmoles) and the ester partition coefficient between octanol and water (3.0) the concentrations were calculated and are presented below in Table II.

TABLE II

| SPECIES/PHASE | INITIAL | | FINAL | |
|---|---|---|---|---|
| | CONC (mM) | mMOLES | CONC (mM) | mMOLES |
| D-ATEE/Org | 1.43 | 1.43 | 1.36 | 1.36 |
| L-ATEE/Org | 1.43 | 1.43 | 0.0 | 0.0 |
| L-AT/Org | 0.0 | 0.0 | — | — |
| D-ATEE/Aq | 0.0 | 0.0 | 0.45 | 0.07 |
| L-ATEE/Aq | 0.0 | 0.0 | 0.0 | 0.0 |
| L-AT/Aq | 0.0 | 0.0 | 9.53 | 1.43 |

Organic phase enantiomeric excess is greater than 99%
Aqueous phase enantiomeric excess = 91%

4.4.16 Example No. 16—Demonstration of BTEE Hydrolysis and Product Enrichment Four grams of Chymotrypsin (Sigma Chemical Co.) were immobilized in a 1 $m^2$ PAN-150 hemofilter (ASAHI Medical Co.) by adsorbing the enzyme on the hollow fibers and then crosslinking the enzyme with a 2.5 % glutaraldehyde solution in 0.05M phosphate buffer pH 7.0.

After loading the enzyme to the reactor, recirculation of 1.07 liters of a 37.7 mM N-benzoyl-L-tyrosine ethyl ester (L-BTEE) in n-octanol solution was started on the shell side. The recirculation rate was 500 ml/min and the average pressure on the shell compartment was kept at 6.5 psi by adjusting a throttling valve at the shell side exit. On the lumen side 0.9 liter of 0.1M $K_2PO_4$ were recirculated at a rate of 500 ml/min. The pH of the aqueous reservoir was kept at 7.8 by addition of NaOH. The reaction progress was monitored by following the caustic consumption. Samples of both, the organic and aqueous phases were taken intermittently and analyzed for the presence of the BTEE and BT acid.

Summary of results at conclusion of experiment:
Total time elapsed: 205 minutes
Initial BTEE concentration in organic: 37.7 mM
Final BTEE concentration in organic: 1.8 mM
Total amount of BTEE hydrolyzed: 38.41 mmoles
Final concentration of BT (product) in aqueous: 187 mM
Total amount of BT (product) in aqueous: 35.5 mmoles
Reactor productivity: 98 moles/yr-$m^2$ As a control experiment 1.1 liters of 40 mM BTEE in octanol were mixed with 0.11 liter of 1M phosphate buffer pH 7.8 using a gear pump in order to obtain a dispersed phase. This dispersion was pumped in a recirculation mode through the shell side of the membrane bioreactor with no flow on the lumen side. The dispersion flowrate was 500 ml/min. After 200 minutes the BTEE concentration in the organic phase was 19.4 mM.

This corresponds to 54% of the conversion that was achieved in the same amount of time in the multiphase membrane bioreactor.

4.4.17 Example No. 17—Glycidyl Butyrate Resolution

A multiphase bioreactor was prepared using a 0.85 m² custom made solvent-resistant membrane module fabricated with polyacrylonitrile, ultrafitration hollow fibers from a PAN-200 hemofilter (Asahi Medical Company). The enzyme, a lipase derived from porcine pancreas, was purchased from Sigma Chemical Company (specific activity 70 units/mg). This enzyme is known to hydrolyze stereoselectively esters of glycidol (a chiral alcohol).

35 grams of the lipase were dissolved in 1 liter of distilled water. The enzyme was loaded into the membrane was previously described in Example No. 1. The shell was filled with hexane to remove any residual water. The lumen was filled with 0.5 liter of potassium phosphate buffer (50 mM, pH 7.8) and recirculated at 250-350 ml/min.

Racemic glycidyl butyrate was synthesized from butyryl chloride and glycidol. The water solubility of the ester is roughly 180 mM. The hexane was drained from the shell and 425 grams of the liquid ester were pumped into the shell. The ester was recirculated at 250-350 ml/min with an outlet pressure of 4-7 psig. The pH of the buffer was controlled at 7.8 with 9.98M KOH.

The reaction rate was monitored by following hydroxide consumption. The average hydrolytic rate for the first 36 minutes was 15,300 umol/min, corresponding to 18.6% conversion of the ester. Samples were periodically withdrawn of both phases. The reaction was stopped after 5.88 hours, corresponding to a 74.7% conversion. The average hydrolytic rate for the run was 6250 umol/min.

The organic samples were mixed with ether, washed with sodium bicarbonate, distilled water and sodium chloride and dried over magnesium sulfate to remove any butyric acid, glycidol and water. The optical resolution of the final glycidyl butyrate sample was $[\alpha]_D = -25.2°$ (c=1, CHCl₃).

4.4.18 Example No. 18—Resolution of Butyl 2-Chloropropionate

Racemic butyl 2-chloropropionate ester was prepared by reacting equimolar amounts of racemic 2-chloropropionic acid with 1-butanol in the presence of acid and continuous removal of water by azeotropic distillation.

An enzyme solution was prepared by dissolving 50 grams of Candida lipase (Sigma Chemical Co.) in water and then filtering this solution. The enzyme was subsequently loaded into a 0.85 m² custom-made solvent-resistant membrane module similar to the one described in Example 1 and in a manner similar to that described in Example 13.

After loading the enzyme in the reactor, recirculation of 500 (3.03 moles) grams of R,S butyl 2-chloropropionate ester on the shell side was started. The recirculation rate was 300 ml/min and the average pressure on the shell compartment was kept at 6.5 psi by adjusting a throttling valve at the shell side exit. On the lumen side 1 liter of 0.05 M phosphate buffer pH 7.0 was recirculated at a rate of 300 ml/min. The reaction was monitored by titrating the aqueous reservoir with 10 N NaOH and maintaining the pH at 7.0.

The reaction was stopped after 60% of the ester was hydrolyzed (10.5 hrs). The remaining organic phase (ester and butanol) was then washed with an equal volume of 1M sodium bicarbonate. The organic phase was determined to be 72.0% ester (w/w) (by HPLC) and had a specific optical rotation of $[\alpha]_D = +5.34°$ (c=1, CHCl₃).

4.4.19 Example No. 19—N-Benzoyl Tyrosine Estrification

An extractive bioreactor was prepared using a 1 m² PAN-150 hemofilter (Asahi Medical Company) containing polyacrylonitrile, ultrafiltration hollow fibers. The enzyme, α-chymotrypsin, was purchased from the Sigma Company (Type II, specific activity 40-60 BTEE units per mg protein).

Three grams of α-chymotrypsin were immobilized in the fibers by adsorbing the enzyme on the fibers and then crosslinking the enzyme with a 2.5% glutaraldehyde solution in 0.05M phosphate buffer pH 7.0.

After loading the enzyme into the reactor, the shell was filled with 200 mls of n-octanol to remove residual water. The recirculation rate was 400 ml/min with an outlet pressure of 6-7 psig. The lumen was rinsed with phosphate buffer and a 50 ml resevoir was setup with a recirculation rate of 400 ml/min. 87 mililiters of ethanol are then introduced to the system. The reaction was then started by replacing the aqueous resevoir with a N-benzoyl-L-tyrosine solution (4.85 gms, 17 mmol of BT in phosphate buffer, pH 6.0). The pH of the aqueous reservoir was controlled at 6.0 with 0.5M HCl.

The reaction was followed by acid consumption. After 120 hours the acid consumption had leveled off and an organic sample was analyzed for N-benzoyl-L-tyrosine ethyl ester (BTEE) by enzymatic hydrolysis with α-chymotrypsin. The BTEE concentration in octanol was 8.7 mM, corresponding to a 10% conversion to ester. It should be noted that without an extracting solvent present, the equilibrium conversion was estimated to be less than 0.1%.

The phase ratio $\theta$ (organic:aqueous) was then increased from $\theta = 1$ to $\theta = 4.5$ by adding 500 ml of octanol and 84 ml of ethanol. After another 105 hours, the BTEE concentration in octanol was 4.8 mM, corresponding to 36% conversion. The increase in extracting solvent shifted the equilibrium conversion higher.

4.4.20 Example No. 20—Ibuprofen Esterification

An extractive bioreactor was prepared using a 0.85 m² custom made solvent-resistant membrane module fabricated with polyacrylonitrile, ultrafiltration hollow fibers from a PAN-200 hemofilter (Asahi Medical Company). The enzyme, a lipase derived from *Candida cylindracea*, was purchased from Genzyme Corporation, with a specific activity of 10500 units per mg. This enzyme is known to stereoselectively hydrolyze esters of Ibuprofen (2-(4-isobutyl phenyl)-propionic acid).

12 grams of the lipase were dissolved in 500 mls of distilled water. This solution was recirculated through the shell with a positive pressure of 3-5 psig. The ultrafiltrate was collected from the lumen side until the reservoir was empty and assayed for residual activity. No significant activity was detected.

One liter of 1-Pentanol was pumped into the shell and recirculated at 300 ml/min with a 5-8 psig outlet pressure. The pentanol will act both as the alcohol donor and the extracting solvent. The lumen was rinsed with 250 ml of potassium phosphate buffer (20 mM, pH 5.5).

A 50 ml reservoir of buffer was established and recirculated at 300 ml/min.

The reaction was started by adding 41 gms of racemic Ibuprofen (dissolved in 100 mls pentanol) to the organic reservoir. After 68 hours, a pentanol sample was analyzed by a Nicolet 5DXC Fourier Transform Infrared Spectrophotometer. An ester was identified by the absorbance at 1735 cm$^{-1}$, indicating enzymatic esterification.

4.4.21 Example No. 21—Phenoxybenzaldehyde Cyanohydrin Hemisuccinate Hydrolysis An extractive bioreactor was prepared using a 0.85 m$^2$ custom-made solvent-resistant membrane module fabricated with polyacrylonitrile, ultrafiltration hollow fibers from a PAN-200 hemofilter (Asahi Medical Company). This type of extractive reactor was run to demonstrate continuous extraction of a chemically liable product into the organic phase. The enzyme a lipase derived from *Chromobacterium viscosum*, was purchased from United States Biochemicals Corporation with a specific activity of 204,000 units per mg.

64 mgs of this enzyme were dissolved in 250 ml of 20 mM potassium phosphate buffer (pH 6.5). This solution was loaded into the membrane as described in Example NO. 2. Spectrophotometric monitoring of the filtrate indicated roughly 50% of the enzyme was retained by the membrane. The shell compartment was then filled with 250 ml of hexane to remove remaining water. The hexane was recirculated at 350-450 ml/min with a 5-7 psig outlet pressure. 300 mls of potassium phosphate buffer (20 mM, pH 6.5) was recirculated through the lumen at 350-450 ml/min.

The half ester f succinic acid and racemic phenoxybenzaldehyde cyanohydrin was synthesized. 1.4 grams of the hemisuccinate ester were dissolved in 20 ml of 4° C. distilled water. The pH was adjusted to 6.4-6.6, with a 1 M solution of dibasic potassium phosphate, to form an aqueous solution of the sodium salt of the ester. The reaction was started by adding the ester solution into the lumen. The pH was controlled at 6.55 with 0.1M NaOH.

Enzymatic hydrolysis of the hemisuccinate ester is known to be stereoselective, producing (S)-phenoxybenzaldehyde cyanohydrin. The cyanohydrin is continuously extracted into the hexane to minimize chemical hydrolysis to achiral phenoxybenzaldehyde and cyanide. After the reaction proceeded for two hours, hydroxide consumption indicated a 48% conversion of the ester to cyanohydrin and succinic acid. The optical rotation of the final hexane phase (Sodium D line, 1 dm path length) was 0.042°. Optical rotation indicates enantiomeric enrichment via enzymatic hydrolysis.

The above description and examples are not intended to limit the spirit or scope of the variety of applications where one might use the disclosed inventive processes.

I claim:

1. A method for resolving a racemic mixture comprising:
   a. providing in a first fluid a racemic mixture having at least a first and second stereoisomer to one side of an enzyme activated membrane wherein said enzyme which activates said membrane catalyzes the reaction of the first stereoisomer into a chiral product having an altered chemical composition;
   b. providing concurrently a second fluid, substantially immiscible in said first fluid, to the opposite side of said enzyme activated membrane, whereby said racemic mixture is resolved with said chiral product of step a principally diffusing into said second fluid from said enzyme activated membrane so that said second fluid predominantly includes said chiral product and said first fluid predominantly includes said second stereoisomer.

2. The method of claim 1 wherein the first fluid is an organic-based solution.

3. The method of claim 1 wherein the second fluid is an aqueous solution.

4. The method of claim 1 wherein the first fluid is an aqueous solution.

5. The method of claim 1 wherein the second fluid is an organic-based solution.

6. The method of claim 1 wherein the reaction of step a is the selected from the group consisting of ester hydrolysis, ester formation, transesterification, transamination, amide hydrolysis, amide formation, hydantoin hydrolysis and nitrile hydrolysis.

7. The method of claim 1 wherein the racemic mixture comprises at least two isomers of an ester.

8. The method of claim 7 wherein the racemic mixture comprises at least two isomers of an ester prepared by reacting an alcohol with a racemic acid.

9. The method of claim 7 wherein the racemic mixture comprises at least two isomers of an ester prepared by reacting an acid with a racemic alcohol.

10. The method of claim 1 wherein the racemic mixture comprises at least two isomers of an amide.

11. The method of claim 10 wherein the racemic mixture comprises at least two isomers of an amide prepared by reacting an amine with a racemic acid.

12. The method of claim 10 wherein the racemic mixture comprises at least two isomers of an amide prepared by reacting an acid with a racemic amine.

13. The method of claim 1 wherein the racemic mixture comprises at least two isomers of a carboxylic acid.

14. The method of claim 1 wherein the racemic mixture comprises at least two isomers of an alcohol.

15. The method of claim 1 wherein the racemic mixture comprises at least two isomers of an amine.

16. The method of claim 1 wherein the racemic mixture comprises at least two isomers of a hydantoin.

17. The method of claim 1 wherein the racemic mixture comprises at least two isomers of a nitrile compound.

18. The method of claim 1 wherein the racemic mixture comprises a compound selected from the group consisting of beta blockers, pheromones, prostaglandins, steroids, flavoring agents, fragrance agents, pharmaceuticals, pesticides, and herbicides.

19. The method of claim 1 wherein the membrane is a hydrophilic membrane.

20. The method of claim 1 wherein the membrane is a microporous membrane.

21. The method of claim 1 wherein the enzyme which activates said membrane is a hydrolytic enzyme.

22. The method of claim 21 wherein the enzyme which activates said membrane is selected from the group consisting of lipases, carboxyl esterases, cholesterol esterase, acetylcholinesterase, peptidases, proteases, trypsin, chymotrypsin, subtilisin, rennin, pepsin, papain, carboxypeptidases, aminopeptidases, amidases, acylases, penicillin acylase, nitrilases, and hydantoinases.

23. The method of claim 1 wherein the enzyme which activates said membrane is bound to a surface of said membrane.

24. The method of claim 1 wherein the enzyme which activates said membrane is bound to both surfaces of said membrane.

25. The method of claim 1 wherein the enzyme which activates said membrane is located within said membrane.

26. The method of claim 1 wherein the enzyme is contained within the pore spaces of an asymmetric and microporous membrane.

27. The method of claim 1 wherein the enzyme is adsorbed on said membrane on the pore wall surfaces of said membrane.

28. The method of claim 1 wherein the enzyme is entrapped within a polymeric gel within pores of said membrane.

29. The method of claim 1 wherein the enzyme is covalently coupled to the pore wall surfaces of said membrane.

30. The method of claim 1 wherein the enzyme is crosslinked within pore spaces of said membrane.

31. The method of claim 1 wherein said enzyme is crosslinked on the pore wall surfaces of said membrane.

32. The method of claim 1 wherein the enzyme is provided in a form selected from the group consisting of purified enzyme, cell extract, cell lysate, partially purified enzyme and whole cells.

33. The method of claim 1 wherein the enzyme is selected from the group consisting of a nitrile hydratase, a transaminase, a oxynitrilase, and a lyase.

34. The method of claim 1 wherein said enzyme is derived from a microorganism.

35. The method of claim 1 wherein the enzyme is derived from a mammal.

36. The method of claim 1 wherein the membrane form is one selected from the group consisting of flat sheet, hollow fiber, and tube.

37. The method of claim 36 wherein the membrane is a skinned, microporous membrane.

38. The method of claim 1 wherein the membrane is constructed of material selected from the group consisting of regenerated cellulose, the esters of cellulose, polyacrylonitrile, polyacrylonitrile copolymers, polyurethane-containing copolymers, polyarylsulfones, polyarylethersulfones, polyarylsulfone blends, polyarylethersulfone blends, polyvinylidene fluoride, polytetrafluoroethylene, polyvinylalcohol, aliphatic polyamides, aromatic polyamides, polyimides, polyetherimides, polyesters, polycarbonates, polyolefins, polybenzimidazole, and polybenzimidazolone.

39. The method of claim 1 wherein the membrane is hydrophobic, one of said first or second fluids is an aqueous solution, and the aqueous solution is under pressure.

40. The method of claim 1 wherein the membrane is hydrophilic, one of said first or second fluids is an organic-based solution, and said organic-based solution is under pressure.

41. The method of claim 3 and 4 wherein the pH of said first fluid ranges from a pH of 2 to about pH 10.

42. The method of claim 41 wherein the pH is between 5.0 and 8.5.

43. The method of claim 1 wherein the reaction takes place at a temperature from about 15° C. to 70° C.

44. The method of claim 43 wherein the said reaction takes place at about 20° C. to about 45° C.

45. The method of claim 1 wherein the chiral product is substantially more soluble in said second fluid than in said first fluid.

46. The method of claim 1 wherein said first and second stereoisomers are substantially more soluble in said first fluid than in said second fluid.

47. The method of claim 1 wherein the first fluid moves in a direction that is countercurrent to said second fluid.

48. The method of claim 1 wherein the racemic mixture comprises at least two stereoisomers of an ester and said chiral product is a carboxylic acid.

49. The method of claim 1 wherein the racemic mixture comprises at least two stereoisomers of an amide and said chiral product is a carboxylic acid.

50. The method of claim 1 wherein said racemic mixture comprises at least two stereoisomers of an ester and said chiral product is an alcohol.

51. The method of claim 1 wherein said racemic mixture comprises at least two steroisomers of an amide and said chiral product is an amine.

52. The method of claim 1 further comprising separating said chiral product from said second fluid.

53. The method of claim 1 further comprising separating said second stereoisomer from said first fluid.

54. The method of claim 1 wherein said first fluid is substantially depleted of said first stereoisomer.

55. The method of claim 1 wherein the racemic mixture is continually recycled to the membrane.

56. The method of claim 1 further comprising removing said first fluid containing the second stereoisomer from said enzyme-activated membrane, racemizing said second stereoisomer, and reintroducing said racemized stereoisomers in the first fluid to said enzyme-activated membrane.

57. The method of claim 1 further comprising removing said second fluid containing said chiral product from the enzyme-activated membrane, racemizing said chiral product, chemically converting said racemized product to the chemical form of said first and second stereoisomers, and reintroducing said racemized stereoisomers in said first fluid to said enzyme-activated membrane.

58. The method of claim 1 wherein the volumetric flowrates of said first fluid and said second fluid flowing past said enzyme-activated membrane differ by a factor from about two to about ten.

59. A method for resolving a racemic mixture comprising:
  a. providing a racemic mixture having at least a first and second stereoisomer in a first fluid to one side of an enzyme activated membrane wherein said enzyme which activates said membrane catalyzes the reaction of the first stereoisomer into a chiral product having an altered chemical composition and a second product and;
  b. providing concurrently a second fluid, substantially immiscible in said first fluid, to the opposite side of said enzyme activated membrane said chiral product of step a principally diffusing into said first fluid from said enzyme activated membrane and said second product principally diffusing into said second fluid, whereby said racemic mixture is resolved with said first fluid containing said second stereoisomer and said chemically distinct chiral product.

60. The method of claim 59 wherein the first fluid is an organic-based solution.

61. The method of claim 59 wherein the second fluid is an aqueous solution.

62. The method of claim 59 wherein the first fluid is an aqueous solution.

63. The method of claim 59 wherein the second fluid is an organic-based solution.

64. The method of claim 59 wherein the reaction of step a is the selected from the group consisting of ester hydrolysis, ester formation, transesterification, transamination, amide hydrolysis, amide formation, hydantoin hydrolysis and nitrile hydrolysis.

65. The method of claim 59 wherein the racemic mixture comprises at least two isomers of an ester.

66. The method of claim 65 wherein the racemic mixture comprises at least two isomers of an ester prepared by reacting an alcohol with a racemic acid.

67. The method of claim 65 wherein the racemic mixture comprises at least two isomers of an ester prepared by reacting an acid with a racemic alcohol.

68. The method of claim 59 wherein the racemic mixture comprises at least two isomers of an amide.

69. The method of claim 68 wherein the racemic mixture comprises at least two isomers of an amide prepared by reacting an amine with a racemic acid.

70. The method of claim 68 wherein the racemic mixture comprises at least two isomers of an amide prepared by reacting an acid with a racemic amine.

71. The method of claim 59 wherein the racemic mixture comprises at least two isomers of a carboxylic acid.

72. The method of claim 59 wherein the racemic mixture comprises at least two isomers of an alcohol.

73. The method of claim 59 wherein the racemic mixture comprises at least two isomers of an amine.

74. The method of claim 59 wherein the racemic mixture comprises at least two isomers of a hydantoin.

75. The method of claim 59 wherein the racemic mixture comprises at least two isomer of a nitrile compound.

76. The method of claim 59 wherein the racemic mixture comprises a compound selected from the group consisting of beta blockers, pheromones, prostaglandins, steroids, flavoring agents, fragrance agents, pharmaceuticals, pesticides, and herbicides.

77. The method of claim 59 wherein the membrane is a hydrophilic membrane.

78. The method of claim 59 wherein the membrane is a microporous membrane.

79. The method of claim 59 wherein the enzyme which activates said membrane is a hydrolytic enzyme.

80. The method of claim 79 wherein the enzyme which activates said membrane is selected from the group consisting of lipases, carboxyl esterases, cholesterol esterase, acetylcholinesterase, peptidases, proteases, trypsin, chymotrypsin, subtilisin, rennin, pepsin, papain, carboxypeptidases, aminopeptidases, amidases, acylases, penicillin acylase, nitrilases, and hydantoinases.

81. The method of claim 59 wherein the enzyme which activates said membrane is bound to a surface of said membrane.

82. The method of claim 59 wherein the enzyme which activates said membrane is bound to both surfaces of said membrane.

83. The method of claim 59 wherein the enzyme which activates said membrane is located within said membrane.

84. The method of claim 59 wherein the enzyme is contained within the pore spaces of an asymmetric and microporous membrane.

85. The method of claim 59 wherein the enzyme is adsorbed on said membrane on the pore wall surfaces of said membrane.

86. The method of claim 59 wherein the enzyme is entrapped within a polymeric gel within pores of said membrane.

87. The method of claim 59 wherein the enzyme is covalently coupled to the pore wall surfaces of said membrane.

88. The method of claim 59 wherein the enzyme is crosslinked within pore spaces of said membrane.

89. The method of claim 59 wherein said enzyme is crosslinked on the pore wall surfaces of said membrane.

90. The method of claim 59 wherein the enzyme is provided in a form selected from the group consisting of purified enzyme, cell extract, cell lysate, partially purified enzyme and whole cells.

91. The method of claim 59 wherein the enzyme is selected from the group consisting of a nitrile hydratase, a transaminase, an oxynitrilase and a lyase.

92. The method of claim 59 wherein said enzyme is derived from a microorganism.

93. The method of claim 59 wherein the enzyme is derived from a mammal.

94. The method of claim 59 wherein the membrane form is one selected from the group consisting of flat sheet, hollow fiber, and tube.

95. The method of claim 94 wherein the membrane is in a skinned, microporous membrane.

96. The method of claim 59 wherein the membrane is constructed of material selected from the group consisting of regenerated cellulose, the esters of cellulose, polyacrylonitrile, polyacrylonitrile copolymers, polyurethane-containing copolymers, polyarylsulfones, polyarylethersulfones, polyarylsulfone blends, polyaryethersulfone blends, polyvinylidene fluoride, polytetrafluoroethylene, polyvinylalcohol, aliphatic polyamide, aromatic polyamides, polyimides, polyesters, polycarbonates, polyetherimides, polyolefins, polybenzimidazole, and polybenzimidazolone.

97. The method of claim 59 wherein the membrane is hydrophobic and the first fluid is an aqueous solution under pressure.

98. The method of claim 59 wherein the membrane is hydrophobic and the second fluid is an aqueous solution under pressure.

99. The method of claim 59 wherein the membrane is hydrophilic, one of said first or second fluids is an organic-based solution, and said organic-based solution is under pressure.

100. The method of claim 61 and 62 wherein the pH of said first fluid ranges from a pH of about 2 to about pH 10.

101. The method of claim 100 wherein the pH is between about 5.0 and about 8.5.

102. The method of claim 59 wherein the reaction takes place at a temperature from about 15° C. to 70° C.

103. The method of claim 102 wherein the said reaction takes place at about 20° C. to about 45° C.

104. The method of claim 59 wherein the chiral product is substantially more soluble in said first fluid than in said second fluid.

105. The method of claim 59 wherein said first and second stereoisomers are substantially more soluble in said first fluid than in said second fluid.

106. The method of claim 59 wherein the first fluid moves in a direction that is countercurrent to said second fluid.

107. The method of claim 59 wherein the racemic mixture comprises at least two stereoisomers of an ester and said chiral product is a carboxylic acid.

108. The method of claim 59 wherein the racemic mixture comprises at least two stereoisomers of an amide and said chiral product is a carboxylic acid.

109. The method of claim 59 wherein said racemic mixture comprises at least two stereoisomers of an ester and said chiral product is an alcohol.

110. The method of claim 59 wherein said racemic mixture comprises at least two stereoisomers of an amide and said chiral product is an amine.

111. The method of claim 59 further comprising separating said chiral product from said first fluid.

112. The method of claim 59 further comprising separating said second stereoisomer from said first fluid.

113. The method of claim 59 wherein said first fluid is substantially depleted of said first stereoisomer.

114. The method of claim 59 wherein the mixture of said second stereoisomer and said chiral product in said first fluid is continually recycled to the membrane.

115. The method of claim 59 further comprising removing said first fluid containing said second stereoisomer and said chiral product from said enzyme-activated membrane, recovering said chiral product from said first fluid, racemizing said second stereoisomer, and reintroducing said racemized stereoisomers in the first fluid to said enzyme-activated membrane.

116. The method of claim 59 wherein the volumetric flowrates past said enzyme-activated membrane of said first fluid and said second fluid differ by a factor of from about two to about ten.

117. A method for producing a chiral product from an achiral precursor comprising:
  a. providing a first fluid containing an achiral precursor to one side of an enzyme activated membrane wherein said enzyme which activates said membrane catalyzes the reaction of said achiral precursor into a chiral product;
  b. providing concurrently a second fluid substantially immiscible in said first fluid, to the opposite side of said enzyme activated membrane said chiral product of step a, principally diffusing into said second fluid from said enzyme activated membrane, whereby said second fluid contains said chiral product.

118. The method of claim 117 wherein the first fluid is an organic-based solution.

119. The method of claim 117 wherein the second fluid is an aqueous solution.

120. The method of claim 117 wherein the first fluid is an aqueous solution.

121. The method of claim 117 wherein the second fluid is an organic-based solution.

122. The method of claim 117 wherein the chiral product is selected from the group consisting of organic acids, alcohols, esters, amides, amines, hydantoins, amino nitriles, pharmaceuticals, fragrance agents, flavoring agents, pheromones, pesticides and herbicides.

123. The method of claim 117 wherein the reaction of step a is the selected from the group consisting of ester hydrolysis, ester formation, transesterification, transamination, amide hydrolysis, amide formation, and nitrile hydrolysis.

124. The method of claim 117 wherein the enzyme which activates said membrane is a hydrolytic enzyme.

125. The method of claim 124 wherein the enzyme is selected from the group consisting of lipases, carboxyl esterases and amidases.

126. The method of claim 117 wherein the reaction of step a is one of asymmetric addition of a chemical moiety across a carbon-to-carbon or carbon-to-oxygen double bond.

127. The method of claim 126 wherein the enzyme which activates said membrane is a lyase.

128. The method of claim 126 wherein the lyase is oxynitrilase or an ammonia lyase.

129. The method of claim 117 wherein the membrane is a hydrophilic membrane.

130. The method of claim 117 wherein the membrane is a microporous membrane.

131. The method of claim 117 wherein the enzyme which activates said membrane is bound to a surface of said membrane.

132. The method of claim 117 wherein the enzyme which activates said membrane is bound to both surfaces of said membrane.

133. The method of claim 117 wherein the enzyme which activates said membrane is located within said membrane.

134. The method of claim 117 wherein the enzyme is contained within the pore spaces of an asymmetric and microporous membrane.

135. The method of claim 117 wherein the enzyme is adsorbed on said membrane on the pore wall surfaces of said membrane.

136. The method of claim 117 wherein the enzyme is entrapped within a polymeric gel within pores of said membrane.

137. The method of claim 117 wherein the enzyme is covalently coupled to the pore wall surfaces of said membrane.

138. The method of claim 117 wherein the enzyme is crosslinked within pore spaces of said membrane.

139. The method of claim 117 wherein said enzyme is crosslinked on the pore wall surfaces of said membrane.

140. The method of claim 117 wherein the enzyme is provided in a form selected from the group consisting of purified enzyme, cell extract, cell lysate, partially purified enzyme and whole cells.

141. The method of claim 117 wherein said enzyme is derived from a microorganism.

142. The method of claim 117 wherein the enzyme is derived from a mammal.

143. The method of claim 117 wherein the membrane form is one selected from the group consisting of flat sheet, hollow fiber and tube.

144. The method of claim 143 wherein the membrane is in a skinned, microporous membrane.

145. The method of claim 117 wherein the membrane is constructed of material selected from the group consisting of regenerated cellulose, the esters of cellulose, polyacrylonitrile, polyacrylonitrile copolymers, polyurethane-containing copolymers, polyarylsulfones, polyarylethersulfones, polyarylsulfone blends, polyaryethersulfone blends, polyvinylidene fluoride, polytetrafluoroethylene, polyvinylalcohol, aliphatic polyamides, aromatic polyamides, polyimides, polyetherimides, polyesters, polycarbonates, polyolefins, polybenzimidazole, and polybenzimidazolone.

146. The method of claim 117 wherein the membrane is hydrophobic, one of said first or second fluids is an aqueous solution, and the aqueous solution is under pressure.

147. The method of claim 117 wherein the membrane is hydrophilic, one of said first or second fluids is an organic-based solution, and said organic-based solution is under pressure.

148. The method of claim 117 wherein the membrane is hydrophilic, one of said first or second fluids is an organic-based solutions, and said organic-based solution is under pressure.

149. The method of claim 119 and 120 wherein the pH of said first fluid ranges from a pH of about 2 to about pH 10.

150. The method of claim 149 wherein the pH is between about 5.0 and about 8.5.

151. The method of claim 117 wherein the reaction takes place at a temperature from about 15° C. to about 70° C.

152. The method of claim 151 wherein the said reaction takes place at about 20° C. to about 45° C.

153. The method of claim 117 wherein the chiral product is substantially more soluble in said second fluid than in said first fluid.

154. The method of claim 117 wherein said achiral precursor is substantially more soluble in said first fluid than in said second fluid.

155. The method of claim 117 wherein the first fluid moves in a direction that is countercurrent to said second fluid.

156. The method of claim 117 further comprising separating said chiral product from said second fluid.

157. The method of claim 117 wherein the volumetric flowrates past said enzyme-activated membrane of said first fluid and said second fluid differ by a factor of from about two to about ten.

* * * * *